US009387264B2

(12) United States Patent
Neeman et al.

(10) Patent No.: US 9,387,264 B2
(45) Date of Patent: Jul. 12, 2016

(54) REPORTER GENES FOR MAGNETIC RESONANCE IMAGING AND METHODS OF USE THEREOF

(71) Applicants: YEDA RESEARCH AND DEVELOPMENT CO. LTD, Rehovot (IL); THE NATIONAL INSTITUTE FOR BIOTECHNOLOGY IN THE NEGEV, Beer Sheva (IL)

(72) Inventors: Michal Neeman, Mazkeret Batya (IL); Raz Zarivach, Beer Sheva (IL); Marina Radoul, Rehovot (IL); Batya Cohen, Rehovot (IL); Moriel Vandsburger, Rehovot (IL); Limor Lewin, D.N Hof Ashkelon (IL)

(73) Assignees: YEDA RESEARCH AND DEVELOPMENT CO. LTD., Rehovot (IL); THE NATIONAL INSTITUTE FOR BIOTECHNOLOGY IN THE NEGEV, Beer Sheva (IL)

( * ) Notice: Subject to any disclaimer, the term of this patent is extended or adjusted under 35 U.S.C. 154(b) by 8 days.

(21) Appl. No.: 13/856,788

(22) Filed: Apr. 4, 2013

(65) Prior Publication Data

US 2013/0280173 A1 Oct. 24, 2013

Related U.S. Application Data

(60) Provisional application No. 61/620,462, filed on Apr. 5, 2012.

(51) Int. Cl.
*A61K 49/14* (2006.01)
*C07K 14/47* (2006.01)
*C07K 14/195* (2006.01)

(52) U.S. Cl.
CPC ............ *A61K 49/14* (2013.01); *C07K 14/195* (2013.01); *C07K 14/47* (2013.01); *C07K 2319/00* (2013.01); *C07K 2319/42* (2013.01)

(58) Field of Classification Search
None
See application file for complete search history.

(56) References Cited

U.S. PATENT DOCUMENTS

| | | | |
|---|---|---|---|
| 4,683,195 | A | 7/1987 | Mullis et al. |
| 7,247,501 | B2 * | 7/2007 | Kim et al. ............... 436/520 |
| 8,084,017 | B2 | 12/2011 | Ahrens |
| 2003/0053949 | A1 * | 3/2003 | Pandey et al. ............ 424/1.11 |
| 2006/0024662 | A1 * | 2/2006 | Ahrens et al. ............ 435/4 |

OTHER PUBLICATIONS

Prozorov et al. Cobalt ferrite nanocrystals: Out-performing magnetotactic bacteria. ACS Nano, vol. 1, No. 3, pp. 228-233, Oct. 2007.*

Amemiya et al.; "Controlled formation of magnetite crystal by partial oxidation of ferrous hydroxide in the presence of recombinant magnetotactic bacterial protein Mms6", Biomaterials 28, 5381-5389, 2007.
Arakaki et al.; "A novel protein tightly bound to bacterial magnetic particles in Magnetospirillum magneticum strain AMB-1", J Biol Chem 278, 8745-8750, 2003.
Arakaki et al.; "Control of the morphology and size of magnetite particles with peptides mimicking the Mms6 protein from magnetotactic bacteria", J Colloid Interface Sci 343, 65-70, 2009.
Bazylinski et al.; Magnetosome formation in prokaryotes, 2004, Nat Rev Microbiol 2, 217-230.
Brooks et al.; "Relaxometry and magnetometry of ferritin", Magn. Reson. Med. 1998; 40: 227-235.
Bulte et al.; "Frequency dependence of MR relaxation times. II. Iron oxides", J. Magn. Reson. Imaging 1993; 3: 641-648.
Bulte et al; "Magnetoferritin: Characterization of a novel superparamagnetic MR contrast agent", JMRI, 4(3): 497-505, 1994.
Caruthers; "Gene Synthesis Machines: DNA Chemistry and Its Uses", (1985) Science 230:281-285.
Cohen et al.; "MRI detection of transcriptional regulation of gene expression in transgenic mice", Nature Medicine, 13(4): 498-503, 2007.
Cohen et al.; "Ferritin as an Endogenous MRI Reporter for Noninvasive Imaging of Gene Expression in C6 Glioma Tumors", Neoplasia, 7:109-117, 2005.
Delano; "The PyMOL Molecular Graphics System", 0.99, 2002, downloaded from http://www.pymol.org/citing and http://www.pymol.org/.
Dong et al.; "Expression and purification of intact and functional soybean (Glycine max) seed ferritin complex in *Escherichia coli*", J Microbiol Biotechnol 18, 299-307, 2008.
Emsley et al.; "Model-building tools for molecular graphics. Acta crystallographica", Section D, Biological crystallography, 60, 2126-32, 2004.
Faivre et al.; "Magnetotactic Bacteria and Magnetosomes", Chem Rev 108, 4875-4898, 2008.
Fischer et al.; "Structural purity of magnetite nanoparticles in magnetotactic bacteria", J R Soc Interface 8, 1011-1018, 2011.
Genove et al.; "A new transgene report for in vivo magnetic resonance imaging", Nature Medicine, 11(4): 450-454, 2005.
Hobbs et al.; "Development of a Bicistronic Vector Driven by the Human Polypeptide Chain Elongation Factor 1α Promoter for Creation of Stable Mammalian Cell Lines That Express Very High Levels of Recombinant Proteins", Biochem Biophys Res Commun., 1998, 252:368-72.

(Continued)

*Primary Examiner* — Jennifer Dunston
(74) *Attorney, Agent, or Firm* — Mark S. Cohen; Pearl Cohen Zedek Latzer Baratz LLP

(57) ABSTRACT

The invention provides a fusion ferritin protein wherein a ferritin heavy chain polypeptide is fused to a peptide, wherein the peptide is fused to the C-terminal end of the ferritin heavy chain; and the peptide includes at least a portion of a Mms6 protein sequence and at least one heterologous amino acid at its N-terminal end. The invention further provides methods of use of the ferritin fusion protein for Magnetic Resonance Imaging.

19 Claims, 11 Drawing Sheets

(56) References Cited

OTHER PUBLICATIONS

Kilcoyne et al.; "Ferritin: a model superparamagnet", J. Magn. & Magn. Mater., 140-144 (1995) 1466.
Maniatis et al., "Molecular Cloning, A Laboratory Manual", 1990, pp. v-I.44.
Meldrum et al.; "Magnetoferritin: in vitro synthesis of a novel magnetic protein" (1992), Science 257, 522-523.
Murat et al.; "Comprehensive genetic dissection of the magnetosome gene island reveals the step-wise assembly of a prokaryotic organelle", Proc Natl Acad Sci U S A 107, 5593-5598, 2010.
Palmer et al.; "Improved System for Helper-Dependent Adenoviral Vector Production", 2003, Mol Ther, 8:846.
Palmer et al.; "Physical and Infectious Titers of Helper-Dependent Adenoviral Vectors: A Method of Direct Comparison to the Adenovirus Reference Material", 2004, Mol Ther, 10:792.
Prozorov et al.; "Protein-mediated synthesis of uniform superparamagnetic magnetite nanocrystals", Adv Funct Mater 17, 951-957, 2007.
Saiki et al.; "Primer-Directed Enzymatic Amplification of DNA with a Thermostable DNA Polymerase", Science, Jan. 29, 1988, 239(4839):487-491).
Sambrook et al.; "Molecular Cloning: A Laboratory Manual", 2nd Edition,1989, pp. v-xii.
Scheffel et al.; "The major magnetosome proteins MamGFDC are not essential for magnetite biomineralization in Magnetospirillum gryphiswaldense but regulate the size of magnetosome crystals", J Bacteriol 190, 377-386, 2008.
Tanaka et al.; "MMS6 Protein Regulates Crystal Morphology during Nano-sized Magnetite Biomineralization in Vivo", Journal of Biological Chemistry 286, 6386-6392, 2011.
Vagin et al.; "REFMAC5 dictionary: organization of prior chemical knowledge and guidelines for its use", Acta Crystallogr D Biol Crystallogr, 60, 2184-2195, 2004.
Zoller; "Iridium Enrichment in Airborne Particles from Kilauea Volcano", Science, Dec. 9, 1983: vol. 222 No. 4628, pp. 1118-1121.
Zoller et al.; "Oligonucleotide-Directed Mutagenesis: A Simple Method Using Two Oligonucleotide Primers and a Single-Stranded DNA Template", (1982; DNA, Dec. 1984;3(6):479-88.

* cited by examiner

| | | | |
|---|---|---|---|
| 1 | MPAQIANGVI | CPPGAPAGTK | AAAAMGEMER | EGAAAKAGAA |
| 41 | KTGAAKTGTV | AKTGIAAKTG | VATAVAAPAA | PANVAAAQGA |
| 81 | GTKVALGAGK | AAAGAKVVGG | TIWTGKGLGL | GLGLGLGAWG |
| 121 | PIILGVVGAG | AVYAYMKSR<u>D</u> | <u>IESAQSDEEV</u> | <u>E</u>LRDALA |
FIGURE 4
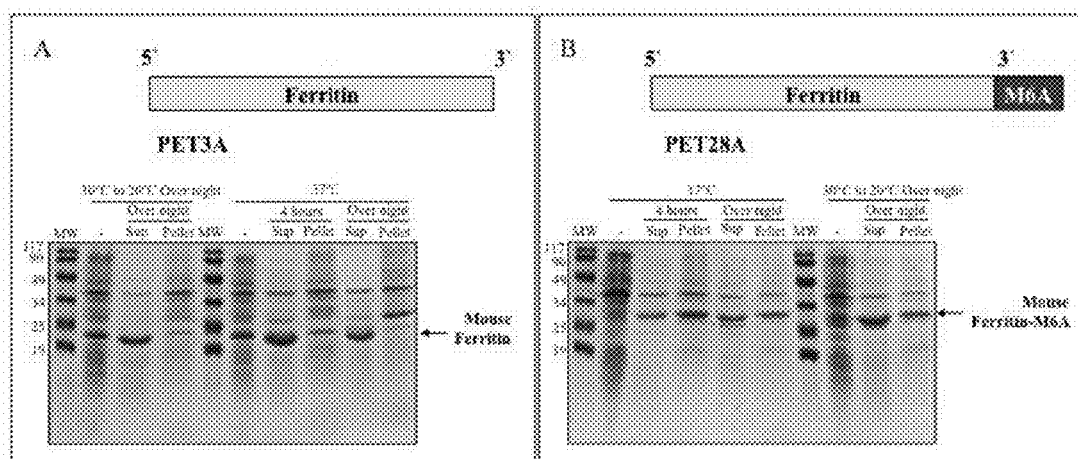
FIGURE 5
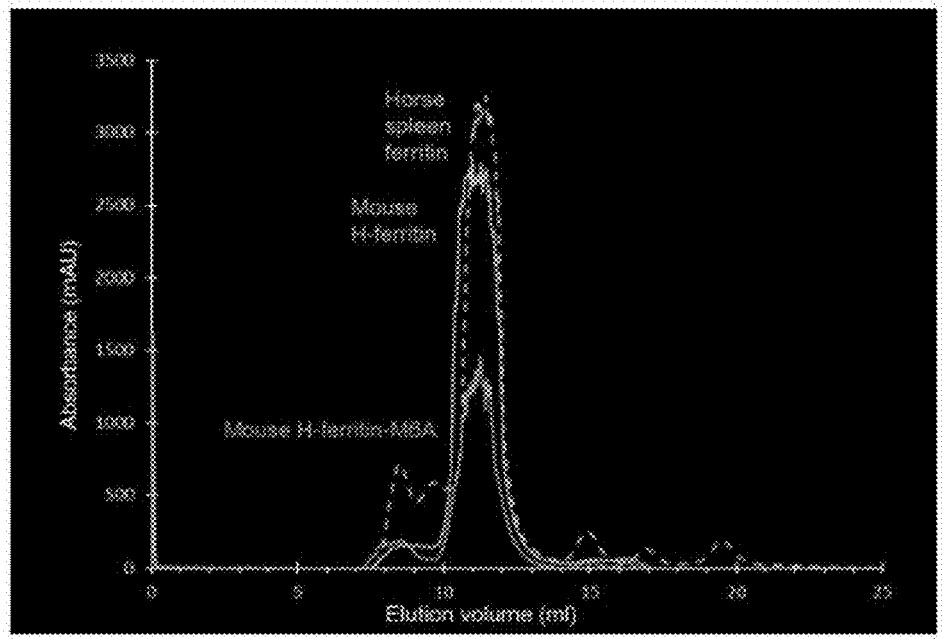
FIGURE 6A

| Crystallization screen | Protein concentration (mg/ml) | Condition |
|---|---|---|
| Index-screen (Hampton Research) | Ferritin-M6A - 10,15 | 0.1M HEPES PH=8.5, 3M NaCl |
| Index-screen (Hampton research) | Ferritin-M6A - 15 | 0.1M BIS-TRIS PH=6.5, 0.2M CaCl2, 25%MPD |
| Index-screen (Hampton research) | Ferritin-M6A - 10,15 | 0.1M BIS-TRIS PH=5.5, 0.2M Ammonium-AC, 45% MPD |
| Index-screen (Hampton research) | Ferritin-M6A - 10,15 | 0.1M HEPES PH=7.5, 0.2M Ammonium-AC, 45% MPD |
| Crystal-screen (Hampton research) | Ferritin-M6A - 20 | 0.1M Tris PH=7.5, 0.2M Ammonium-AC, 30% 2-Propanol |
| Crystal-screen (Hampton research) | Ferritin-M6A - 20 | 0.1M Na-Cacodylate PH=6.5, 0.2M Mg-AC, 30% MPD |
| Crystal-screen (Hampton research) | Ferritin-M6A - 20 | 0.1M HEPES PH=7.5, 0.2M MgCl2, 30% PEG400 |
| Crystal-screen (Hampton research) | Ferritin-M6A - 20 | 0.1M HEPES PH=7-7.5, 0.2M CaCl2, 25%-30% PEG400 |
| Crystal-screen (Hampton research) | Ferritin-M6A - 20 | 0.1M HEPES PH=7.5, 1.4M Tri-Na-Citrate, 30% 2-Propanol |
| Crystal-screen (Hampton research) | Ferritin - 20 | 0.1M Na-Cacodylate PH=6.5, 0.2M Tri-Na-Citrate |
| Crystal-screen (Hampton research) | Ferritin - 20 | 0.1M Tris PH=8.5/9, 0.2M Tri-Na-Citrate, 30% PEG400 |

FIGURE 18

| Crystallization screen | Protein concentration (mg/ml) | Condition |
|---|---|---|
| Crystal-screen (Hampton research) | Ferritin - 20 | 0.1M Tri-Na-Citrate PH= 5.6, 0.2M Ammonium-AC, 30% MPD |
| Crystal-screen (Hampton research) | Ferritin - 20 | 0.1M Na-AC PH=4.6, 2M Na-Formate |
| Crystal-screen (Hampton research) | Ferritin - 20 | 0.1M Tris PH=8.5, 25% MPD |
| Crystal-screen (Hampton research) | Ferritin - 20 | 0.1M Na-Cacodylate PH=6.5, 0.2M CaAC, 18% PEG400 |
| WIZARD (EMERALD BIO) | Ferritin-M6A - 20 | 0.1M Na-K-Phosphate PH=5.4/5.7/6.2, 35%MPD 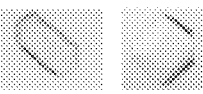 |
| WIZARD (EMERALD BIO) | Ferritin-M6A - 15,20 | 0.1M Na-AC PH=4.5, 0.2M Ca-AC, 30% PEG400  |
| WIZARD (EMERALD BIO) | Ferritin-M6A - 20 | 0.1M Na-AC PH=4.5, 30% MPD |
| WIZARD (EMERALD BIO) | Ferritin - 20 | 0.1M Na-K-Phosphate PH=6.2, 2.5M NaCl  |
| WIZARD (EMERALD BIO) | Ferritin - 20 | 0.1M Na-K-Phosphate PH=6.2, 35% MPD |
| WIZARD (EMERALD BIO) | Ferritin - 20 | 0.1M Na-AC PH=4.5, 0.2M Ca-AC, 30% PEG400 |

FIGURE 18 (CONT.)

ND METHODS OF USE THEREOF

SEQUENCE LISTING

```
<160> NUMBER OF SEQ ID NOS: 26

<210> SEQ ID NO 1
<211> LENGTH: 157
<212> TYPE: PRT
<213> ORGANISM: Magnetospirillum magneticumstrain
<220> FEATURE:
<221> NAME/KEY: misc_feature
<223> OTHER INFORMATION: AMB1 Mms6

<400> SEQUENCE: 1

Met Pro Ala Gln Ile Ala Asn Gly Val Ile Cys Pro Pro Gly Ala Pro
1               5                   10                  15

Ala Gly Thr Lys Ala Ala Ala Ala Met Gly Glu Met Glu Arg Glu Gly
            20                  25                  30

Ala Ala Ala Lys Ala Gly Ala Ala Lys Thr Gly Ala Ala Lys Thr Gly
        35                  40                  45

Thr Val Ala Lys Thr Gly Ile Ala Ala Lys Thr Gly Val Ala Thr Ala
```

```
                50                 55                  60
Val Ala Pro Ala Ala Pro Ala Asn Val Ala Ala Gln Gly Ala
 65              70                  75                  80

Gly Thr Lys Val Ala Leu Gly Ala Gly Lys Ala Ala Gly Ala Lys
                 85                  90                  95

Val Val Gly Gly Thr Ile Trp Thr Gly Lys Gly Leu Gly Leu
            100                 105                 110

Gly Leu Gly Leu Gly Ala Trp Gly Pro Ile Ile Leu Val Val Gly
            115                 120                 125

Ala Gly Ala Val Tyr Ala Tyr Met Lys Ser Arg Asp Ile Glu Ser Ala
            130                 135                 140

Gln Ser Asp Glu Glu Val Glu Leu Arg Asp Ala Leu Ala
145                 150                 155

<210> SEQ ID NO 2
<211> LENGTH: 12
<212> TYPE: PRT
<213> ORGANISM: Magnetospirillum Magneticumstrain
<220> FEATURE:
<221> NAME/KEY: misc_feature
<223> OTHER INFORMATION: 12 aa peptide from Mms6

<400> SEQUENCE: 2

Asp Ile Glu Ser Ala Gln Ser Asp Glu Glu Val Glu
1               5                  10

<210> SEQ ID NO 3
<211> LENGTH: 13
<212> TYPE: PRT
<213> ORGANISM: Artificial Sequence
<220> FEATURE:
<223> OTHER INFORMATION: M6A with G

<400> SEQUENCE: 3

Gly Asp Ile Glu Ser Ala Gln Ser Asp Glu Glu Val Glu
1               5                  10

<210> SEQ ID NO 4
<211> LENGTH: 182
<212> TYPE: PRT
<213> ORGANISM: Mus musculus
<220> FEATURE:
<221> NAME/KEY: misc_feature
<223> OTHER INFORMATION: mouse Heavy chain-ferritin

<400> SEQUENCE: 4

Met Thr Thr Ala Ser Pro Ser Gln Val Arg Gln Asn Tyr His Gln Asp
1               5                  10                  15

Ala Glu Ala Ala Ile Asn Arg Gln Ile Asn Leu Glu Leu Tyr Ala Ser
                20                  25                  30

Tyr Val Tyr Leu Ser Met Ser Cys Tyr Phe Asp Arg Asp Asp Val Ala
            35                  40                  45

Leu Lys Asn Phe Ala Lys Tyr Phe Leu His Gln Ser His Glu Glu Arg
 50                  55                  60

Glu His Ala Glu Lys Leu Met Lys Leu Gln Asn Gln Arg Gly Gly Arg
 65                  70                  75                  80

Ile Phe Leu Gln Asp Ile Lys Lys Pro Asp Arg Asp Asp Trp Glu Ser
                 85                  90                  95

Gly Leu Asn Ala Met Glu Cys Ala Leu His Leu Glu Lys Ser Val Asn
            100                 105                 110
```

```
Gln Ser Leu Leu Glu Leu His Lys Leu Ala Thr Asp Lys Asn Asp Pro
            115                 120                 125

His Leu Cys Asp Phe Ile Glu Thr Tyr Tyr Leu Ser Glu Gln Val Lys
    130                 135                 140

Ser Ile Lys Glu Leu Gly Asp His Val Thr Asn Leu Arg Lys Met Gly
145                 150                 155                 160

Ala Pro Glu Ala Gly Met Ala Glu Tyr Leu Phe Asp Lys His Thr Leu
                165                 170                 175

Gly His Gly Asp Glu Ser
            180

<210> SEQ ID NO 5
<211> LENGTH: 192
<212> TYPE: PRT
<213> ORGANISM: Artificial Sequence
<220> FEATURE:
<223> OTHER INFORMATION: mouse HA- H-ferritin

<400> SEQUENCE: 5

Met Ala Tyr Pro Tyr Asp Val Pro Asp Tyr Met Thr Thr Ala Ser Pro
1               5                   10                  15

Ser Gln Val Arg Gln Asn Tyr His Gln Asp Ala Glu Ala Ala Ile Asn
            20                  25                  30

Arg Gln Ile Asn Leu Glu Leu Tyr Ala Ser Tyr Val Tyr Leu Ser Met
        35                  40                  45

Ser Cys Tyr Phe Asp Arg Asp Asp Val Ala Leu Lys Asn Phe Ala Lys
    50                  55                  60

Tyr Phe Leu His Gln Ser His Glu Glu Arg Glu His Ala Glu Lys Leu
65                  70                  75                  80

Met Lys Leu Gln Asn Gln Arg Gly Gly Arg Ile Phe Leu Gln Asp Ile
                85                  90                  95

Lys Lys Pro Asp Arg Asp Asp Trp Glu Ser Gly Leu Asn Ala Met Glu
            100                 105                 110

Cys Ala Leu His Leu Glu Lys Ser Val Asn Gln Ser Leu Leu Glu Leu
        115                 120                 125

His Lys Leu Ala Thr Asp Lys Asn Asp Pro His Leu Cys Asp Phe Ile
    130                 135                 140

Glu Thr Tyr Tyr Leu Ser Glu Gln Val Lys Ser Ile Lys Glu Leu Gly
145                 150                 155                 160

Asp His Val Thr Asn Leu Arg Lys Met Gly Ala Pro Glu Ala Gly Met
                165                 170                 175

Ala Glu Tyr Leu Phe Asp Lys His Thr Leu Gly His Gly Asp Glu Ser
            180                 185                 190

<210> SEQ ID NO 6
<211> LENGTH: 205
<212> TYPE: PRT
<213> ORGANISM: Artificial Sequence
<220> FEATURE:
<223> OTHER INFORMATION: mouse HA-ferritin-M6A (with G)

<400> SEQUENCE: 6

Met Ala Tyr Pro Tyr Asp Val Pro Asp Tyr Met Thr Thr Ala Ser Pro
1               5                   10                  15

Ser Gln Val Arg Gln Asn Tyr His Gln Asp Ala Glu Ala Ala Ile Asn
            20                  25                  30

Arg Gln Ile Asn Leu Glu Leu Tyr Ala Ser Tyr Val Tyr Leu Ser Met
        35                  40                  45
```

Ser Cys Tyr Phe Asp Arg Asp Val Ala Leu Lys Asn Phe Ala Lys
         50                  55                  60

Tyr Phe Leu His Gln Ser His Glu Glu Arg Glu His Ala Glu Lys Leu
 65                  70                  75                  80

Met Lys Leu Gln Asn Gln Arg Gly Gly Arg Ile Phe Leu Gln Asp Ile
                 85                  90                  95

Lys Lys Pro Asp Arg Asp Asp Trp Glu Ser Gly Leu Asn Ala Met Glu
            100                 105                 110

Cys Ala Leu His Leu Glu Lys Ser Val Asn Gln Ser Leu Leu Glu Leu
            115                 120                 125

His Lys Leu Ala Thr Asp Lys Asn Asp Pro His Leu Cys Asp Phe Ile
130                 135                 140

Glu Thr Tyr Tyr Leu Ser Glu Gln Val Lys Ser Ile Lys Glu Leu Gly
145                 150                 155                 160

Asp His Val Thr Asn Leu Arg Lys Met Gly Ala Pro Glu Ala Gly Met
                165                 170                 175

Ala Glu Tyr Leu Phe Asp Lys His Thr Leu Gly His Gly Asp Glu Ser
            180                 185                 190

Gly Asp Ile Glu Ser Ala Gln Ser Asp Glu Glu Val Glu
            195                 200                 205

<210> SEQ ID NO 7
<211> LENGTH: 195
<212> TYPE: PRT
<213> ORGANISM: Artificial Sequence
<220> FEATURE:
<223> OTHER INFORMATION: mouse ferritin heavy chain fused to M6A (with
      G); no tag

<400> SEQUENCE: 7

Met Thr Thr Ala Ser Pro Ser Gln Val Arg Gln Asn Tyr His Gln Asp
 1               5                  10                  15

Ala Glu Ala Ala Ile Asn Arg Gln Ile Asn Leu Glu Leu Tyr Ala Ser
            20                  25                  30

Tyr Val Tyr Leu Ser Met Ser Cys Tyr Phe Asp Arg Asp Asp Val Ala
         35                  40                  45

Leu Lys Asn Phe Ala Lys Tyr Phe Leu His Gln Ser His Glu Glu Arg
 50                  55                  60

Glu His Ala Glu Lys Leu Met Lys Leu Gln Asn Gln Arg Gly Gly Arg
 65                  70                  75                  80

Ile Phe Leu Gln Asp Ile Lys Lys Pro Asp Arg Asp Asp Trp Glu Ser
                 85                  90                  95

Gly Leu Asn Ala Met Glu Cys Ala Leu His Leu Glu Lys Ser Val Asn
            100                 105                 110

Gln Ser Leu Leu Glu Leu His Lys Leu Ala Thr Asp Lys Asn Asp Pro
            115                 120                 125

His Leu Cys Asp Phe Ile Glu Thr Tyr Tyr Leu Ser Glu Gln Val Lys
130                 135                 140

Ser Ile Lys Glu Leu Gly Asp His Val Thr Asn Leu Arg Lys Met Gly
145                 150                 155                 160

Ala Pro Glu Ala Gly Met Ala Glu Tyr Leu Phe Asp Lys His Thr Leu
                165                 170                 175

Gly His Gly Asp Glu Ser Gly Asp Ile Glu Ser Ala Gln Ser Asp Glu
            180                 185                 190

Glu Val Glu

<210> SEQ ID NO 8
<211> LENGTH: 942
<212> TYPE: DNA
<213> ORGANISM: Mus musculus
<220> FEATURE:
<221> NAME/KEY: misc_feature
<223> OTHER INFORMATION: mouse ferritin heavy chain cDNA

<400> SEQUENCE: 8

```
agcgctcgcc tgacgcagga tcccgctata agtgcggccc gctgtcccct cctgcgccag    60
acgttctcgc ccagagtcgc cgcggttccc tgcttcaaca gtgcttgaac ggaacccggt   120
gctcgacccc tccgaccccc gccggccgct tcgagcctga gccctttgca acttcgtcgt   180
tccgccgctc cagcgtcgcc accgcgcctc gccccgccgc caccatgacc accgcgtctc   240
cctcgcaagt gcgccagaac taccaccagg acgcggaggc tgccatcaac cgccagatca   300
acctggagtt gtatgcctcc tacgtctatc tgtctatgtc ttgttatttt gaccgagatg   360
atgtggctct gaagaacttt gccaaatact ttctccacca atctcatgag gagagggagc   420
atgccgagaa actgatgaag ctgcagaacc agcgaggtgg ccgaatcttc ctgcaggata   480
taaagaaacc agaccgtgat gactgggaga gcgggctgaa tgcaatggag tgtgcactgc   540
acttggaaaa gagtgtgaat cagtcactac tggaactgca caaactggct actgacaaga   600
atgatcccca cttatgtgac ttcattgaga cgtattatct gagtgaacag gtgaaatcca   660
ttaaagaact gggtgaccac gtgaccaact acgcaagat gggtgcccct gaagctggca   720
tggcagaata tctctttgac aagcacaccc tgggacacgg tgatgagagc taagctgact   780
tccccaaagc cacgtgactt tactggtcac tgaggcagtg catgcatgtc aggctgcctt   840
catcttttct ataagttgca ccaaaacatc tgcttaagtt ctttaatttg taccatttct   900
tcaaataaag aattttggta cccagcttct tttctttgtg at                      942
```

<210> SEQ ID NO 9
<211> LENGTH: 6
<212> TYPE: DNA
<213> ORGANISM: Unknown
<220> FEATURE:
<223> OTHER INFORMATION: Kozak sequence nucleotide

<400> SEQUENCE: 9 gaggcc    6

<210> SEQ ID NO 10
<211> LENGTH: 183
<212> TYPE: PRT
<213> ORGANISM: Homo sapiens
<220> FEATURE:
<221> NAME/KEY: misc_feature
<223> OTHER INFORMATION: Human Ferritin heavy chain amino acid
       AAA52437.1; AAA52438.1; AAA35833.1; AAF89523.1; NP_002023.2

<400> SEQUENCE: 10

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
            20                  25                  30

Tyr Val Tyr Leu Ser Met Ser Tyr Tyr Phe Asp Arg Asp Asp Val Ala
        35                  40                  45

Leu Lys Asn Phe Ala Lys Tyr Phe Leu His Gln Ser His Glu Glu Arg

```
                50                  55                  60

Glu His Ala Glu Lys Leu Met Lys Leu Gln Asn Gln Arg Gly Gly Arg
 65                  70                  75                  80

Ile Phe Leu Gln Asp Ile Lys Lys Pro Asp Cys Asp Asp Trp Glu Ser
                 85                  90                  95

Gly Leu Asn Ala Met Glu Cys Ala Leu His Leu Glu Lys Asn Val Asn
                100                 105                 110

Gln Ser Leu Leu Glu Leu His Lys Leu Ala Thr Asp Lys Asn Asp Pro
                115                 120                 125

His Leu Cys Asp Phe Ile Glu Thr His Tyr Leu Asn Glu Gln Val Lys
130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Ser
                180

<210> SEQ ID NO 11
<211> LENGTH: 56
<212> TYPE: PRT
<213> ORGANISM: Homo sapiens
<220> FEATURE:
<221> NAME/KEY: misc_feature
<223> OTHER INFORMATION: Human Ferritin heavy chain amino acid, partial
      AAA52479.1

<400> SEQUENCE: 11

Pro His Leu Cys Asp Phe Ile Glu Thr His Tyr Leu Asn Glu Gln Val
 1               5                  10                  15

Lys Ala Ile Lys Glu Leu Gly Asp His Val Thr Asn Leu Arg Lys Met
                20                  25                  30

Gly Ala Pro Glu Ser Gly Leu Ala Glu Tyr Leu Phe Asp Lys His Thr
            35                  40                  45

Leu Gly Asp Ser Asp Asn Glu Ser
    50                  55

<210> SEQ ID NO 12
<211> LENGTH: 183
<212> TYPE: PRT
<213> ORGANISM: Homo sapiens
<220> FEATURE:
<221> NAME/KEY: misc_feature
<223> OTHER INFORMATION: Human Ferritin-like heavy chain amino acid
      Q9BXU8.1

<400> SEQUENCE: 12

Met Ala Thr Ala Gln Pro Ser Gln Val Arg Gln Lys Tyr Asp Thr Asn
 1               5                  10                  15

Cys Asp Ala Ala Ile Asn Ser His Ile Thr Leu Glu Leu Tyr Thr Ser
                20                  25                  30

Tyr Leu Tyr Leu Ser Met Ala Phe Tyr Phe Asn Arg Asp Asp Val Ala
            35                  40                  45

Leu Glu Asn Phe Phe Arg Tyr Phe Leu Arg Leu Ser Asp Lys Met
 50                  55                  60

Glu His Ala Gln Lys Leu Met Arg Leu Gln Asn Leu Arg Gly Gly His
 65                  70                  75                  80

Ile Cys Leu His Asp Ile Arg Lys Pro Glu Cys Gln Gly Trp Glu Ser
                85                  90                  95
```

```
Gly Leu Val Ala Met Glu Ser Ala Phe His Leu Glu Lys Asn Val Asn
            100                 105                 110

Gln Ser Leu Leu Asp Leu Tyr Gln Leu Ala Val Glu Lys Gly Asp Pro
        115                 120                 125

Gln Leu Cys His Phe Leu Glu Ser His Tyr Leu His Glu Gln Val Lys
    130                 135                 140

Thr Ile Lys Glu Leu Gly Gly Tyr Val Ser Asn Leu Arg Lys Ile Cys
145                 150                 155                 160

Ser Pro Glu Ala Gly Leu Ala Glu Tyr Leu Phe Asp Lys Leu Thr Leu
                165                 170                 175

Gly Gly Arg Val Lys Glu Thr
            180
```

<210> SEQ ID NO 13
<211> LENGTH: 183
<212> TYPE: PRT
<213> ORGANISM: Homo sapiens
<220> FEATURE:
<221> NAME/KEY: misc_feature
<223> OTHER INFORMATION: Recombinant Human Ferritin-like heavy chain
      amino acid (point mutations)

<400> SEQUENCE: 13

```
Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
            20                  25                  30

Tyr Val Tyr Leu Ser Met Ser Tyr Tyr Phe Asp Arg Asp Asp Val Ala
        35                  40                  45

Leu Lys Asn Phe Ala Lys Tyr Phe Leu His Gln Ser His Glu Glu Arg
    50                  55                  60

Glu His Ala Glu Lys Leu Met Lys Leu Gln Asn Gln Arg Gly Gly Arg
65                  70                  75                  80

Ile Phe Leu Gln Asp Ile Gln Lys Pro Asp Cys Asp Asp Trp Glu Ser
                85                  90                  95

Gly Leu Asn Ala Met Glu Cys Ala Leu His Leu Asp Lys Asn Val Asn
            100                 105                 110

Gln Ser Leu Leu Glu Leu His Lys Leu Ala Thr Asp Lys Asn Asp Pro
        115                 120                 125

His Leu Cys Asp Phe Ile Glu Thr His Tyr Leu Asn Glu Gln Val Lys
    130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Ser
            180
```

<210> SEQ ID NO 14
<211> LENGTH: 183
<212> TYPE: PRT
<213> ORGANISM: Homo sapiens
<220> FEATURE:
<221> NAME/KEY: misc_feature
<223> OTHER INFORMATION: Recombinant Human Ferritin-like heavy chain
      amino acid (point mutations)

<400> SEQUENCE: 14

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Asp Leu Tyr Ala Ser
                20                  25                  30

Tyr Val Tyr Leu Ser Met Ser Tyr Tyr Phe Asp Arg Asp Asp Val Ala
            35                  40                  45

Leu Lys Asn Phe Ala Lys Tyr Phe Leu His Gln Ser His Glu Glu Arg
        50                  55                  60

Glu His Ala Glu Lys Leu Met Lys Leu Gln Asn Gln Arg Gly Gly Arg
65                  70                  75                  80

Ile Phe Leu Gln Asp Ile Gln Lys Pro Asp Cys Asp Asp Trp Glu Ser
                85                  90                  95

Gly Leu Asn Ala Met Glu Cys Ala Leu His Leu Asp Lys Asn Val Asn
            100                 105                 110

Gln Ser Leu Leu Glu Leu His Lys Leu Ala Thr Asp Lys Asn Asp Pro
        115                 120                 125

His Leu Cys Asp Phe Ile Glu Thr His Tyr Leu Asn Glu Gln Val Lys
    130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Ser
            180

<210> SEQ ID NO 15
<211> LENGTH: 49
<212> TYPE: PRT
<213> ORGANISM: Homo sapiens
<220> FEATURE:
<221> NAME/KEY: misc_feature
<223> OTHER INFORMATION: Human Ferritin-like heavy chain amino acid,
      partial CAP19952.1

<400> SEQUENCE: 15

Ser Tyr Tyr Phe Asp Arg Asp Asp Val Ala Leu Lys Asn Phe Ala Lys
1               5                   10                  15

Tyr Phe Leu His Gln Ser His Glu Glu Arg Glu His Ala Glu Lys Leu
                20                  25                  30

Met Lys Leu Gln Asn Gln Arg Gly Gly Arg Ile Phe Leu Gln Asp Ile
            35                  40                  45

Lys

<210> SEQ ID NO 16
<211> LENGTH: 183
<212> TYPE: PRT
<213> ORGANISM: Homo sapiens
<220> FEATURE:
<221> NAME/KEY: misc_feature
<223> OTHER INFORMATION: Human Ferritin-like heavy chain amino acid,
      BAG54435.1

<400> SEQUENCE: 16

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
                20                  25                  30

Tyr Val Tyr Leu Ser Met Ser Tyr Tyr Phe Asp Arg Asp Asp Val Ala
            35                  40                  45

Leu Lys Asn Phe Ala Lys Tyr Phe Leu His Gln Ser His Glu Glu Arg
 50                  55                  60

Glu His Ala Glu Lys Leu Met Lys Leu Gln Asn Gln Arg Gly Gly Arg
 65                  70                  75                  80

Ile Phe Leu Gln Asp Ile Lys Lys Pro Asp Cys Asp Asp Trp Glu Gly
                 85                  90                  95

Gly Leu Asn Ala Met Glu Cys Ala Leu His Leu Glu Lys Asn Val Asn
                100                 105                 110

Gln Ser Leu Leu Glu Leu His Lys Leu Ala Thr Asp Lys Asn Asp Pro
            115                 120                 125

His Leu Cys Asp Phe Ile Glu Thr His Tyr Leu Asn Glu Gln Val Lys
130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Ser
            180

<210> SEQ ID NO 17
<211> LENGTH: 182
<212> TYPE: PRT
<213> ORGANISM: Homo sapiens
<220> FEATURE:
<221> NAME/KEY: misc_feature
<223> OTHER INFORMATION: Human Ferritin-llike heavy chain amino acid,
      3AJO_A

<400> SEQUENCE: 17

Thr Thr Ala Ser Thr Ser Gln Val Arg Gln Asn Tyr His Gln Asp Ser
 1               5                  10                  15

Glu Ala Ala Ile Asn Arg Gln Ile Asn Leu Glu Leu Tyr Ala Ser Tyr
             20                  25                  30

Val Tyr Leu Ser Met Ser Tyr Tyr Phe Asp Arg Asp Asp Val Ala Leu
         35                  40                  45

Lys Asn Phe Ala Lys Tyr Phe Leu His Gln Ser His Glu Glu Arg Glu
 50                  55                  60

His Ala Glu Lys Leu Met Lys Leu Gln Asn Gln Arg Gly Gly Arg Ile
 65                  70                  75                  80

Phe Leu Gln Asp Ile Lys Lys Pro Asp Cys Asp Asp Trp Glu Ser Gly
                 85                  90                  95

Leu Asn Ala Met Glu Cys Ala Leu His Leu Glu Lys Asn Val Asn Gln
                100                 105                 110

Ser Leu Leu Glu Leu His Lys Leu Ala Thr Asp Lys Asn Asp Pro His
            115                 120                 125

Leu Cys Asp Phe Ile Glu Thr His Tyr Leu Asn Glu Gln Val Lys Ala
130                 135                 140

Ile Lys Glu Leu Gly Asp His Val Thr Asn Leu Arg Lys Met Gly Ala
145                 150                 155                 160

Pro Glu Ser Gly Leu Ala Glu Tyr Leu Phe Asp Lys His Thr Leu Gly
                165                 170                 175

Asp Ser Asp Asn Glu Ser
            180

<210> SEQ ID NO 18
<211> LENGTH: 1245

```
<212> TYPE: DNA
<213> ORGANISM: Homo sapiens
<220> FEATURE:
<221> NAME/KEY: misc_feature
<223> OTHER INFORMATION: Human Ferritin-like heavy chain nucleic acid,
      NM_002032.2

<400> SEQUENCE: 18
ataagagacc acaagcgacc cgcagggcca gacgttcttc gccgagagtc gtcggggttt      60
cctgcttcaa cagtgcttgg acggaacccg gcgctcgttc cccacccggg ccggccgccc     120
atagccagcc ctccgtcacc tcttcaccgc accctcggac tgccccaagg ccccgccgc      180
cgctccagcg ccgcgcagcc accgccgccg ccgccgcctc ccttagtcg ccgccatgac      240
gaccgcgtcc acctcgcagg tgcgccagaa ctaccaccag gactcagagg ccgccatcaa     300
ccgccagatc aacctggagc tctacgcctc ctacgtttac ctgtccatgt cttactactt     360
tgaccgcgat gatgtggctt tgaagaactt tgccaaatac tttcttcacc aatctcatga     420
ggagagggaa catgctgaga aactgatgaa gctgcagaac caacgaggtg gccgaatctt     480
ccttcaggat atcaagaaac cagactgtga tgactgggag agcgggctga atgcaatgga     540
gtgtgcatta catttggaaa aaaatgtgaa tcagtcacta ctggaactgc acaaactggc     600
cactgacaaa aatgaccccc atttgtgtga cttcattgag acacattacc tgaatgagca     660
ggtgaaagcc atcaaagaat gggtgaccac cgtgaccaac ttgcgcaaga tgggagcgcc     720
cgaatctggc ttggcggaat atctctttga caagcacacc ctgggagaca gtgataatga     780
aagctaagcc tcgggctaat ttccccatag ccgtggggtg acttccctgg tcaccaaggc     840
agtgcatgca tgttggggtt tcctttacct tttctataag ttgtaccaaa acatccactt     900
aagttctttg atttgtacca ttccttcaaa taaagaaatt tggtacccag tgttgtctt      960
tgaggtcttg ggatgaatca gaaatctatc caggctatct tccagattcc ttaagtgccg    1020
ttgttcagtt ctaatcacac taatcaaaaa gaaacgagta tttgtattta ttaaactcat    1080
tagtttgggc agtatactaa ggtgtggctg tcttggattc agatagaact aagggttccc    1140
gactctgaat ccagagtctg agttaaatgt ttccaatggt tcagtctagc tttcacagtt    1200
tttatgaata aaaggcatta aaggctgaaa aaaaaaaaa aaaaa                     1245

<210> SEQ ID NO 19
<211> LENGTH: 171
<212> TYPE: DNA
<213> ORGANISM: Homo sapiens
<220> FEATURE:
<221> NAME/KEY: misc_feature
<223> OTHER INFORMATION: Human Ferritin-like heavy chain nucleic acid,
      partial M15383.1

<400> SEQUENCE: 19
ccccatttgt gtgacttcat tgagacacat tacctgaatg agcaggtgaa agccatcaaa      60
gaattgggtg accacgtgac caacttgcgc aagatgggag cgcccgaatc tggcttggcg     120
gaatatctct ttgacaagca caccctggga gacagtgata atgaaaagcta a             171

<210> SEQ ID NO 20
<211> LENGTH: 1197
<212> TYPE: DNA
<213> ORGANISM: Homo sapiens
<220> FEATURE:
<221> NAME/KEY: misc_feature
<223> OTHER INFORMATION: Human ferritin-like heavy chain nucleic acid,
      L20941.1
```

<400> SEQUENCE: 20

```
cagacgttct tcgccgagag tcgtcggggt ttcctgcttc aacagtgctt ggacggaacc    60
cggcgctcgt tccccacccc ggccggccgc ccatagccag ccctccgtca cctcttcacc   120
gcaccctcgg actgccccaa ggccccgcc gccgctccag cgccgcgcag ccaccgccgc    180
cgccgccgcc ctctccttag tcgccgccat gacgaccgcg tccacctcgc aggtgcgcca   240
gaactaccac caggactcag aggccgccat caaccgccag atcaacctgg agctctacgc   300
ctcctacgtt tacctgtcca tgtcttacta ctttgaccgc gatgatgtgg ctttgaagaa   360
ctttgccaaa tactttcttc accaatctca tgaggagagg gaacatgctg agaaactgat   420
gaagctgcag aaccaacgag gtggccgaat cttccttcag gatatcaaga aaccagactg   480
tgatgactgg gagagcgggc tgaatgcaat ggagtgtgca ttacatttgg aaaaaaatgt   540
gaatcagtca ctactggaac tgcacaaact ggccactgac aaaaatgacc cccatttgtg   600
tgacttcatt gagacacatt acctgaatga gcaggtgaaa gccatcaaag aattgggtga   660
ccacgtgacc aacttgcgca agatgggagc gcccgaatct ggcttggcgg aatatctctt   720
tgacaagcac accctgggag acagtgataa tgaaagctaa gcctcgggct aatttcccca   780
tagccgtggg gtgacttccc tggtcaccaa ggcagtgcat gcatgttggg gtttcctttta  840
ccttttctat aagttgtacc aaaacatcca cttaagttct ttgatttgta ccattcttca   900
aataaagaaa tttggtaccc aggtgttgtc tttgaggtct tggatgaatc agaaatctat   960
ccaggctatc ttccagattc cttaagtgcc gttgttcagt tctaatcaca ctaatcaaaa  1020
agaaacgagt atttgtattt attaaactat tagtttgggc agtatactaa ggtgtggctg  1080
tcttggattc agatagaact aagggttccc gactctgaat ccagagtctg agttaaatgt  1140
ttccaatggt tcagtctagc tttcacagtt tttatgaata aaaggcatta aaggctg     1197
```

<210> SEQ ID NO 21
<211> LENGTH: 1119
<212> TYPE: DNA
<213> ORGANISM: Homo sapiens
<220> FEATURE:
<221> NAME/KEY: misc_feature
<223> OTHER INFORMATION: Human Ferritin-like heavy chain nucleic acid, M97164.1

<400> SEQUENCE: 21

```
cggccggccg cccatagcca gccctccgtc acctcttcac cgcaccctcg gactgcccca    60
aggccccgc cgccgctcca gcgccgcgca gccaccgccg ccgccgccgc cctctcctta   120
gtcgccgcca tgacgaccgc gtccacctcg caggtgcgcc agaactacca ccaggactca   180
gaggccgcca tcaaccgcca gatcaacctg gagctctacg cctcctacgt ttacctgtcc   240
atgtcttact actttgaccg cgatgatgtg gctttgaaga actttgccaa atactttctt   300
caccaatctc atgaggagag ggaacatgct gagaaactga tgaagctgca gaaccaacga   360
ggtggccgaa tcttccttca ggatatcaag aaaccagact gtgatgactg ggagagcggg   420
ctgaatgcaa tggagtgtgc attacatttg gaaaaaaatg tgaatcagtc actactggaa   480
ctgcacaaac tggccactga caaaaatgac ccccatttgt gtgacttcat tgagacacat   540
tacctgaatg agcaggtgaa agccatcaaa gaattgggtg accacgtgac caacttgcgc   600
aagatgggag cgcccgaatc tggcttggcg gaatatctct ttgacaagca caccctggga   660
gacagtgata atgaaagcta agcctcgggc taatttcccc atagccgtgg ggtgacttcc   720
ctggtcacca aggcagtgca tgcatgttgg gtttcctttt accttttcta taagttgtac   780
```

-continued

| caaaacatcc acttaagttc tttgatttgt accattcttc aaataaagaa atttggtacc | 840 |
| caggtgttgt ctttgaggtc ttggatgaat cagaaatcta tccaggctat cttccagatt | 900 |
| ccttaagtgc cgttgttcag ttctaatcac actaatcaaa aagaaacgag tatttgtatt | 960 |
| tattaaactc attagtttgg gcagtatact aaggtgtggc tgtcttggat tcagatagaa | 1020 |
| ctaagggttc ccgactctga atccagagtc tgagttaaat gttccaatg gttcagtcta | 1080 |
| gctttcacag tttttatgaa taaaaggcat taaaggctg | 1119 |

<210> SEQ ID NO 22
<211> LENGTH: 790
<212> TYPE: DNA
<213> ORGANISM: Homo sapiens
<220> FEATURE:
<221> NAME/KEY: misc_feature
<223> OTHER INFORMATION: Human Ferritin-like heavy chain nucleic acid, M11146.1

<400> SEQUENCE: 22

| actgccccaa ggcccccgcc gccgctccag cgccgcgcag ccaccgccgc cgccgccgcc | 60 |
| tctccttagt cgccgccatg acgaccgcgt ccacctcgca ggtgcgccag aactaccacc | 120 |
| aggactcaga ggccgccatc aaccgccaga tcaacctgga gctctacgcc tcctacgttt | 180 |
| acctgtccat gtcttactac tttgaccgcg atgatgtggc tttgaagaac tttgccaaat | 240 |
| actttcttca ccaatctcat gaggagaggg aacatgctga gaaactgatg aagctgcaga | 300 |
| accaacgagg tggccgaatc ttccttcagg atatcaagaa accagactgt gatgactggg | 360 |
| agagcgggct gaatgcaatg gagtgtgcat tacatttgga aaaaaatgtg aatcagtcac | 420 |
| tactggaact gcacaaactg gccactgaca aaaatgaccc ccatttgtgt gacttcattg | 480 |
| agacacatta cctgaatgag caggtgaaag ccatcaaaga attgggtgac cacgtgacca | 540 |
| acttgcgcaa gatgggagcg cccgaatctg gcttggcgga atatctcttt gacaagcaca | 600 |
| ccctgggaga cagtgataat gaaagctaag cctcgggcta atttccccat agccgtgggg | 660 |
| tgacttccct ggtcaccaag gcagtgcatg catgttgggg tttcctttac cttttctata | 720 |
| agttgtacca aacatccac ttaagttctt tgatttgtac cattccttca aataaagaaa | 780 |
| tttggtaccc | 790 |

<210> SEQ ID NO 23
<211> LENGTH: 708
<212> TYPE: DNA
<213> ORGANISM: Homo sapiens
<220> FEATURE:
<221> NAME/KEY: misc_feature
<223> OTHER INFORMATION: Human Ferritin-like heavy chain nucleic acid, AF088851.1

<400> SEQUENCE: 23

| gctccagcgc cgcgcagcca ccgcctctcc ttagtcgccg ccatgacgac cgcgtccacc | 60 |
| tcgcaggtgc gccagaacta ccaccaggac tcagaggccg ccatcaaccg ccagatcaac | 120 |
| ctggagctct acgcctccta cgtttacctg tccatgtctt actactttga ccgcgatgat | 180 |
| gtggctttga gaactttgc caaatacttt cttcaccaat ctcatgagga gagggaacat | 240 |
| gctgagaaac tgatgaagct gcagaaccaa cgaggtggcc gaatcttcct tcaggatatc | 300 |
| aagaaaccag actgtgatga ctgggagagc gggctgaatg caatggagtg tgcattacat | 360 |
| ttggaaaaaa atgtgaatca gtcactactg gaactgcaca aactggccac tgacaaaaat | 420 |

| | |
|---|---|
| gaccccccatt tgtgtgactt cattgagaca cattacctga atgagcaggt gaaagccatc | 480 |
| aaagaattgg gtgaccacgt gaccaacttg cgcaagatgg gagcgcccga atctggcttg | 540 |
| gcggaatatc tctttgacaa gcacaccctg ggagacagtg ataatgaaag ctaagcctcg | 600 |
| ggctaatttc cccatagccg tggggtgact tccctggtca ccaaggcagt gcatgcggat | 660 |
| cccccaatca ctagacggcc gcctgcaggt cgaccatagg gagagctg | 708 |

<210> SEQ ID NO 24
<211> LENGTH: 3621
<212> TYPE: DNA
<213> ORGANISM: Homo sapiens
<220> FEATURE:
<221> NAME/KEY: misc_feature
<223> OTHER INFORMATION: Human Ferritin-like heavy chain nucleic acid, highly similar AK127090.1

<400> SEQUENCE: 24

| | |
|---|---|
| agaggcgggc agaggcggcg agaggcggcg agaggcgggc tgaggcgccc cagcggcggc | 60 |
| aggtaggcgc ggccgcgatg ctcgcgcgcg ggccggggcc caggagctcc cccgtgccgg | 120 |
| gcaaggggc gacctcgggg tccgcgctct caccccacc ccgcccactt tgtccatcag | 180 |
| gtccgggggc gccggggca tggactagcc ttctcgaccc cgagcgggcc ccaccgaggg | 240 |
| ctcccgagag ccagccgcgc ccctccgcgc cctcgcatac ctggctgccc agtctcgtct | 300 |
| cccccggtcc ggcccggcgc ccacccgtcg ggctgccctc aggggctggg ctcgggccag | 360 |
| gagatggctg cgccggcggc caagcccggt ccgggtataa atagctcggt ccgcggtggc | 420 |
| gggggcgcg ggctatattt ggtggggctg ctgcagccct ccctgtatgg gtggcctccc | 480 |
| cgagggagtg gggagcactt cgcgctcggc cgtggcgctt tcccctgttc gcaacaccct | 540 |
| gaacactccc cgaccacac ccgcccttgg gcaatgacta acagcccgag accgtgcagg | 600 |
| gaagtggggg accctctcca gagccaggct gggctccctg ggttcgccct acctccaccc | 660 |
| ctggccccca gctcgtggga aaaccagacg cagcctttgg tagcctccca cttcctaacc | 720 |
| cacgcctcag tttccctata cgaaaagtgg gttggtcagg agcctccctg ggtgttgggc | 780 |
| cagtcaagag acaggagccg cagagtggaa gggaagccct tagctctggc cggggcctcc | 840 |
| aggggtggct ggagtcggtg agggacgatg ggggagccg aggggcggct gtcctcctct | 900 |
| ctgtcccaga ggcatgggct gaaagggtcc ctctcctggt gatggccaga gtcaggcctg | 960 |
| ctgggcggga atggcagtt ggcccacccc aaggcccagg ggcttgtcca tgctgagcac | 1020 |
| aagggtggga ggtcttgtgt ctgttggggc cggggagtcc aaggtcccag cttcactgca | 1080 |
| caggcctgga agtcaggtgg gtgctggcct gaccctgctg aaggagggtc tattccgcca | 1140 |
| gcgtggtgtg gaggcggctg ggctcgactc cctcatggag ggaaggaact gaggaggtgc | 1200 |
| taggaggccg tgggggggtg tctgccccca gagaggcttt gagtgcatgg gggctctgcc | 1260 |
| gtggcacgtg cagcgtctgt cccccagggc cccatggtgt ggacagagtc tggggtgggc | 1320 |
| acctggaggc ctggtctcaa ggcaggcttg gtaacgaccc catgtgacct tgggcagggc | 1380 |
| ccgccatcca ggccacccag aaagccatgt ggcctgcacg atcaggccag accccactga | 1440 |
| ctggagcggg gcactttact ttggaggggc agctaccaga gggctctatg atcccagcc | 1500 |
| cagccgtcag gccggacggg tccccctac tggcctgcag tgacccttat gccaggctcg | 1560 |
| gctggctcag cggtgggtcc tgggtgacc tggccacgtg ggacagaagg gcctgtgccg | 1620 |
| ctcccctccag tgaggtgcca aatgtgggcc acactctggg cccagcgggg ggccttccgg | 1680 |
| gcagtggcgc agagccattg gaggtgcccg ggccctgggg caggggcggg gcgggagcag | 1740 |

```
acagagctca gggcgtcctc ctagcgtcac ctgcccgagt caggcccatc tgtgaaatgg    1800
gccacgccgg gcagcctcac gcaacggaac cgaaccgccg ggctcctgct ccagacccg     1860 cagttcacga gtcgacgccc ccgagtcccg agccgcgccc actggtccca cctctgcagc    1920
aagtggagtc ggccccgccc tgtggcttcg aggcccgac gcctggcgcg gctcccgggc     1980
tccgctgacc ccggtggacc cgcgcgccgg caattacggt agcgtccagt agggcgccta    2040
ctgcgggcaa tacgggggct cctcccatgg cgcggtcacg tccccacgt cccgcggctg     2100 gcggggcggg gccgggcgga gcatccttcc ctcccctcc cccgggtggg cccgcccag      2160 cctcgaccac ccgcgccgac ccccgcccgc agagccggga agccggaacc cgcaggcgcc    2220
ctccagccgt ccctccggcc cgggcgggga ttgcgccgag aggggcctc tcctggcgag     2280 ggtggagttt tgggttcccc ccttcgcccc gcacctcccg ccttcctgcc tcctcccggt    2340
cttcaccttc cccccgggt ccccacgacg cccgctgggc ggcggtgggg taggggcgc      2400 ctcctgaccc gactcccctt ccagccttgg ccttcaggca ctggctttag ggtggagggg    2460
cggccttgcg gggtccagga ggcctcggag gtggggacg gcggctctgg accagctccg     2520
gcccccacca cctcccggcc ccagggcggt gacagccttg cggagaaggg gtcttcaaag    2580
ctctgagacc ccgcagtgcc agctcaggat tgaagcctgc ggcggacat gcagccttcc     2640 tttcccaaag gggacttgcg cccagcccct cttgggcac cagtgggggc tcctggccct     2700
ggccctgggt gggagtggcc aatccgcaaa tgaggcctgt gtgtctgccc cgccggcccc    2760
tgccgtcgtg atgtaagcgg acacagagcg gcagggcacg ggctgcgcga ggggtctgcg    2820
ggggtcagag gtggggcgca aggcccccgc cgccgctcca gcgccgcgca gccaccgccg    2880
ccgccgccgc ctctccttag tcgccgccat gacgaccgcg tccacctcgc aggtgcgcca    2940
gaactaccac caggactcag aggccgccat caaccgccag atcaacctgg agctctacgc    3000
ctcctacgtt tacctgtcca tgtcttacta ctttgaccgc gatgatgtgg ctttgaagaa    3060 cttttgccaaa tactttcttc accaatctca tgaggagagg gaacatgctg agaaactgat    3120
gaagctgcag aaccaacgag gtggccgaat cttccttcag gatatcaaga agccagactg    3180
tgatgactgg gagggcgggc tgaatgcaat ggagtgtgca ttcacatttgg aaaaaaatgt    3240 gaatcagtca ctactggaac tgcacaaact ggccactgac aaaaatgacc cccatttgtg    3300
tgacttcatt gagacacatt acctgaatga gcaggtgaaa gccatcaaag aatttgggtga    3360 ccacgtgacc aacttgcgca agatgggagc gccccgaatct ggcttggcgg aatatctctt    3420
tgacaagcac accctgggag acagtgataa tgaaagctaa gcctcgggct aatttccca     3480 tagccgtggg gtgacttccc tggtcaccaa ggcagtgcat gcatgttggg gtttccttta    3540 cctttctat aagttgtacc aaaacatcca cttaagttct tgatttgta ccattccttc       3600 aaataaagaa atttggtacc c                                              3621
```

<210> SEQ ID NO 25
<211> LENGTH: 2166
<212> TYPE: DNA
<213> ORGANISM: Homo sapiens
<220> FEATURE:
<221> NAME/KEY: misc_feature
<223> OTHER INFORMATION: Human Ferrittin-like haevy chain nucleic acid, highly similar AK054816.1

<400> SEQUENCE: 25

```
gcatttgtgc ctgaagctgc cgggtctgct acggcaccgc ggggctgcag aaacccgggg    60
```

| | |
|---|---|
| gccaagggcg ggctgcttgc cgctatggct ggcagtcagg acatattcga tgccatcgtg | 120 |
| atggcggatg agaggtttca tggggaaggg tatcgggaag gctatgaaga aggcagtagt | 180 |
| ttgggtgtga tggagggaag gcagcatggc acgctgcatg gagccaaaat cgggtctgag | 240 |
| atcgggtgct accaaggttt tgcttttgca tggaaatgtc tactgcacag ttgcaccact | 300 |
| gagaaggaca gcagaaagat gaaggtctta gaatcattga ttggaatgat ccagaaattc | 360 |
| ccttatgatg accctactta cgataaactc catgaagact agacaagat cagaggaaaa | 420 |
| tttaaacagt tttgttcgtt actcaatgtt cagccagact ttaaaattag tgcagaaggt | 480 |
| tccggacttt cattttgagg aggatggatg aacagagacc gaacgtcgag gaacagatgt | 540 |
| gtgtggacgt gtttagaaat gcggtgaagg gccagacggt gctgggaagg cagttgttca | 600 |
| ttgggagggt gagggttccg gttcggccgt gggagggctt ccttccctgg ggttttctgc | 660 |
| ctgtgtcacc ttggtgcccg tcttggggcc tctccacaca tgccctttgt tgggctgaag | 720 |
| ccgtccctgg cagagccctc gtgcattgac ttgacagcct ctccggcagc acaggcctag | 780 |
| ctggttctgg gttggagttg gctctggata gggttagtca ccaggcctgg actgaaggca | 840 |
| gttatttta ttattattat tatttgcaat gagagagatg gttggccccg aatgaggctc | 900 |
| atgggaggtt tggacgggtg ctgtgccgca tgtcgaggcc gattgtgtgc caggcggtgc | 960 |
| gggacgtgcc tcccgtgtgt tatttaatcc cttcaggagc ccacaagatg ggtgttattc | 1020 |
| tcattttaca gaggagggag gggagacgcg aagggattgc ctggtctaag ggcacccagc | 1080 |
| agcagagcta ggacttccgc cctaaggctg tgcctcactg ccaccaggca cagccgcctc | 1140 |
| cggaatgcac aggcgagtcc ctgccctccc tcccaggccg cacaggtcct gccaagcctc | 1200 |
| acggagcacg ggggagtctg tggtggccag tttacctggg catctggaga cgttcttcgc | 1260 |
| cgagagtcgt cggggtttcc tgcttcaaca gtgcttggac ggaacccggc gctcgttccc | 1320 |
| caccccggcc ggccgcccat agccagccct ccgtcacctc ttcaccgcac cctcggactg | 1380 |
| ccccaaggcc cccgccgccg ctccagcgcc gcgcagccac cgccgccgcc gccgcctctc | 1440 |
| cttagtcgcc gccatgacga ccgcgtccac ctcgcaggtg cgccagaact accaccagga | 1500 |
| ctcagaggcc gccatcaacc gccagatcaa cctggagctc tacgcctcct acgtttacct | 1560 |
| gtccatgtct tactactttg accgcgatga tgtggctttg aagaactttg ccaaatactt | 1620 |
| tcttcaccaa tctcatgagg agagggaaca tgctgagaaa ctgatgaagc tgcagaacca | 1680 |
| acgaggtggc cgaatcttcc ttcaggatat caagaaacca gactgtgatg actgggagag | 1740 |
| cgggctgaat gcaatggagt gtgcattaca tttggaaaaa aatgtgaatc agtcactact | 1800 |
| ggaactgcac aaactggcca ctgacaaaaa tgaccccat ttgtgtgact tcattgagac | 1860 |
| acattacctg aatgagcagg tgaaagccat caaagaattg ggtgaccacg tgaccaactt | 1920 |
| gcgcaagatg ggagcgcccg aatctggctt ggcggaatat ctctttgaca agcacaccct | 1980 |
| gggagacagt gataatgaaa gctaagcctc gggctaattt cccatagcc gtggggtgac | 2040 |
| ttccctggtc accaaggcag tgcatgcatg ttggggtttc cttacctttt tctataagtt | 2100 |
| gtaccaaaac atccacttaa gttctttgat ttgtaccatt ccttcaaata agaaatttg | 2160 |
| gtaccc | 2166 |

<210> SEQ ID NO 26
<211> LENGTH: 2034
<212> TYPE: DNA

<213> ORGANISM: Homo sapiens
<220> FEATURE:
<221> NAME/KEY: misc_feature
<223> OTHER INFORMATION: Human Ferritin-like heavy chain nucleic acid,
      highly similar AK095899.1

<400> SEQUENCE: 26

| | | | | | |
|---|---|---|---|---|---|
| gcgccttcgg | ctcgcgcgcg | ccctccgcg | gcggctccac | cgcccgggat | ggtacggtcc | 60 |
| ggcagccggg | ccgcgcgctg | ccgcccctcg | gtgagctggt | gtgggccgcc | gctagcggag | 120 |
| acgacccttt | ccactcgcgt | ggtgccgtgg | tctgcaaatg | aagagtccag | aaaagaagcg | 180 |
| aaggaagtca | aatactcagg | gccctgcata | ctcacatctg | acggagtttg | caccaccccc | 240 |
| aactcccatg | gtggatcacc | tggttgcatc | caaccctttt | gaagatgact | cggagcccc | 300 |
| caaagtgggg | gttgcagccc | ctccattcct | tggcagtcct | gtgcccttcg | gaggcttccg | 360 |
| tgtgcagggg | ggcatggcgg | gccaggtacc | cccaggctac | agcactggag | gtggaggggg | 420 |
| cccccagcca | ctccgtcgac | agccaccccc | cttccctccc | aatcctatgg | gccctgcttt | 480 |
| caacatgccc | cccagggtc | ctggctaccc | accccaggc | aacatgaact | tcccagcca | 540 |
| acccttcaac | cagcctctgg | gtcaaaactt | tagtcctccc | agtgggcaga | tgatgccggg | 600 |
| cccagtgggg | ggatttggtc | ccatgatctc | acccaccatg | ggacagcctc | ccagagcaga | 660 |
| gctgggccca | ccttctctgt | cccaacgatt | tgctcagcca | ggggctcctt | ttggcccttc | 720 |
| tcctctccag | agacctggtc | aggggctccc | cagcctgccg | cctaacacaa | gtccctttcc | 780 |
| tggtccggac | cctggctttc | ctggccctgg | tggtgaggat | ggggggaagc | ccttgaatcc | 840 |
| acctgcttct | actgcttttc | cccaggagcc | ccactcaggc | tccccggctg | ctgctgttaa | 900 |
| tgggaaccag | cccagtttcc | ccccgaacag | cagtgggcgg | ggtgggggca | ctccagatgc | 960 |
| caacagcttg | gcaccccctg | gcaaggcagg | tgggggctcc | gggcccccagc | ctccccagg | 1020 |
| cttggtgtac | ccatgtggtg | cctgtcggag | tgaggtgaac | gatgaccagg | atgccattct | 1080 |
| gtgtgaggcc | tcctgccaga | aatggttcca | ccgtgagtgc | acaggcatga | ctgagagcgc | 1140 |
| ctatgggctg | ctgaccactg | aagcttctgc | cgtctgggcc | tgcgatctct | gcctcaagac | 1200 |
| caaggagatc | cagtctgtct | acatccgtga | gggcatgggg | cagctggtgg | ctgctaacga | 1260 |
| tgggtgacgc | tggtgaagtg | gcccagggaa | gtgcacatgt | ctctccttag | tcgccgccat | 1320 |
| gacgaccgcg | tccacctcgc | aggtgcgcca | gaactaccac | caggactcag | aggccgccat | 1380 |
| caaccgccag | atcaacctgg | agctctacgc | ctcctacgtt | tacctgtcca | tgtcttacta | 1440 |
| ctttgaccgc | gatgatgtgg | ctttgaagaa | ctttgccaaa | tactttcttc | accaatctca | 1500 |
| tgaggagagg | gaacatgctg | agaaactgat | gaagctgcag | aaccaacgag | gtggccgaat | 1560 |
| cttccttcag | gatatcaaga | aaccagactg | tgatgactgg | gagagcgggc | tgaatgcaat | 1620 |
| ggagtgtgca | ttcactttgg | aaaaaaatgt | gaatcagtca | ctactggaac | tgcacaaact | 1680 |
| ggccactgac | aaaaatgacc | cccatttgtg | tgacttcatt | gagacacatt | acctgaatga | 1740 |
| gcaggtgaaa | gccatcaaag | aattgggtga | ccacgtgacc | aacttgcgca | agatgggagc | 1800 |
| gcccgaatct | ggcttggcgg | aatatctctt | tgacaagcac | accctgggag | acagtgataa | 1860 |
| tgaaagctaa | gcctcgggct | aatttccca | tagccgtggg | gtgacttccc | tggtcaccaa | 1920 |
| ggcagtgcat | gcatgttggg | gtttccttta | ccttttctat | aagttgtacc | aaaacatcca | 1980 |
| cttaagttct | ttgatttgta | ccattccttc | aaataaagaa | atttggtacc | cagg | 2034 |

REPORTER GENES FOR MAGNETIC RESONANCE IMAGING AND METHODS OF USE THEREOF

CROSS REFERENCE TO RELATED APPLICATIONS

This application claims priority from U.S. Provisional Application Ser. No. 61/620,462, filed Apr. 5, 2012, which is incorporated in its entirety herein by reference.

FIELD OF THE INVENTION

This invention is directed to recombinant nucleic acids encoding ferritin fusion proteins and the use of these ferritin fusion proteins as reporter agents for Magnetic Resonance Imaging (MRI).

BACKGROUND OF THE INVENTION

Noninvasive molecular imaging methods are used to provide noninvasive dynamic information on gene expression, transcriptional regulation of gene expression, and tumor microenvironment and the consequences of chemo- and/or radiation therapy.

For example oxygen deficiency, or hypoxia, is a central microenvironmental tumor stress that arises as a consequence of the expansion of solid tumors by cancer cell proliferation, which is unmatched by the expansion and maintenance of the vasculature supply. Tumor cells surrounding functional blood vessels are generally better oxygenated, and tumor cells distant from blood vessels are poorly oxygenated. The irregular blood flow in tumors exposes tumor cells not only to chronic hypoxia, but also to acute hypoxia in regions with intermittent blood flow. Hypoxia has been recognized to induce gene instability, and also to provide an important selective pressure resulting in increased tumor aggressiveness and resistance to hypoxia-induced apoptosis. Hypoxia also leads to tumor resistance to radiation and chemotherapy treatment regimes. Hypoxia has been demonstrated in clinical trials to be associated with a poor prognosis. Accordingly, knowledge of the hypoxic state of a tumor may influence clinical treatment decisions.

Noninvasive molecular imaging methods may also be used for tracking cell location and differentiation in vivo following cellular based therapies including stem cell therapies, bone marrow transplantation, gene therapy and immune cell therapies. Such information aids scientists in biological and preclinical research, as well as providing guidance during gene therapy and in detecting, and monitoring the fate of cells during clinical treatment.

Noninvasive molecular imaging of dynamic processes has benefited tremendously from the use of reporter genes. These genes encode for proteins that emit light, bind radio-labeled probes or modulate MRI contrast. Reporter genes play a pivotal role in monitoring cell trafficking, gene replacement therapy, protein-protein interactions, neuronal plasticity, and embryonic development. To serve as a reporter gene, it is important to show not only that the encoded polypeptide can be detected in a manner that would faithfully correlate spatially and temporally with information to be gained, for example, transcription regulation or hypoxic state of a tumor microenvironment, but also that the reporter expression in the cells of interest will not alter the fate of the cells.

MRI reporter genes have the advantage that the specific signal can be coregistered with soft-tissue anatomy and functional tissue information and have, therefore, become an active and growing area of scientific interest. Several strategies exist for generating MRI contrast: using enzyme-catalyzed chemical modification of metal-based contrast agents or (phosphorus) metabolites, iron-binding and iron-storage proteins to accumulate iron as a contrast agent, and artificial proteins for imaging based on chemical exchange saturation transfer.

Current MRI reporter genes include creatine kinase, tyrosinase, β-galactosidase, transferrin receptor, ferritin, the bacterial iron transporter Mag A and a lysine-rich protein (LRP). The disadvantages of these current reporters include low resolution imaging, signal dependency on availability of iron, false signal generation, difficulties with accessibility and nonspecific uptake of substrate nanoparticles, delay of change in signal that is dependent on iron availability and ferritin loading factor, and low sensitivity.

For example, ferritin is the main iron storage and controlled-release protein in mammals, which plays a key role in the iron metabolism of mammals. Ferritin forms a highly symmetrical spherical polypeptide shell, termed a "ferritin particle", able to store up to 4500 iron atoms as non-magnetic nanocrystal of ferrihydrite in its core (FIG. 1). Ferrihydrite is found in the core of ferritin.

Due to this paramagnetic core, ferritin exhibits magnetic properties and has recently proposed as MRI reporter gene, see for example U.S. Pat. No. 8,084,017, which is incorporated herein in its entirety. The iron moments in each ferritin core tend to align antiferromagnetically, where almost all spins cancel as pairs of aligned in opposite directions spins. Thus, net core magnetic moments (up to 300 μB) arise from uncompensated spins at the surface of the core.

However, compared to superparamagnetic iron oxides (8000-63000 μB), native ferritin has a relatively low $R_2$ relaxivity and thus provides relatively low sensitivity as MRI contrast agent. Considering, that iron oxide form can be converted to magnetite and maghemite ($\gamma$-$Fe_2O_3$) within the ferritin core through oxygen reduction and heating (magnetite), followed by oxidation (maghemite), one way to increase sensitivity of ferritin is to convert the ferrihydrite in its core into magnetite as has been done chemically, to form magnetoferritin.

Magnetite can also be generated biologically. Magnetotactic bacteria, which mineralize iron into a particular iron oxide, serve as an example of such process. In these microorganisms, the biomineralization of iron takes place in the magnetosome, a specialized subcellular organelle, assembled from a chain of bilayer lipid invaginations that each induce the deposition of—and enclose—a ~50 nm crystal of magnetite ($Fe_3O_4$) or its sulfide analog, greigite ($Fe_3S_4$) (FIG. 2).

The magnetosome expresses unique sets of soluble and integral-membrane magnetosome associated proteins (MAPs) that are essential for magnetite formation. Specifically, it has been shown that Mms6 interacts directly with magnetite.

Mms6 is a small acidic MAP that contains a Leu-Gly-rich motif. Of the whole set of magnetosome-associated proteins that are linked to magnetite biomineralization, Mms6 (FIG. 4) is the only protein that has been shown in vitro to undergo proteolytic processing from its pre-protein (~136 amino acids) to its active form (~77 amino acids). This active component, being tightly bound to the magnetite surface, is able to interact directly with magnetite. It has been predicted that the active component of Mms6 is a peptide composed of a non-structured hydrophobic tail attached to a C-terminal α-helical portion. It has been demonstrated that Mms6 interacts with magnetite via its α-helical C-terminus. It has also been found that Mms6 deletion in vivo yielded a deformed magnetite crystal with additional crystal faces that are not present in the magnetite of wild-type bacteria.

SUMMARY OF THE INVENTION

In one embodiment, this invention provides a nucleic acid sequence encoding a recombinant ferritin heavy chain fusion protein, comprising a nucleic acid sequence encoding a ferritin heavy chain polypeptide fused to a peptide, wherein said peptide is fused to the C-terminal end of said ferritin heavy chain; said peptide comprising at least a portion of a Mms6 protein sequence and at least one heterologous amino acid at its N-terminal end.

In one embodiment, this invention provides a vector comprising a ferritin fusion protein.

In one embodiment, this invention provides a host cell comprising a vector comprising a ferritin fusion protein.

In one embodiment, this invention provides a recombinant ferritin heavy chain fusion protein, said fusion protein comprising a ferritin heavy chain polypeptide fused to a peptide, wherein said peptide is fused to the C-terminal end of said ferritin heavy chain; said peptide comprising at least a portion of a Mms6 protein sequence and at least one heterologous amino acid at its N-terminal end.

In one embodiment, this invention provides a Magnetic Resonance Imaging (MRI) contrast agent useful for providing increased contrast in an image of a biological sample comprising: (a) an isolated, recombinant fusion protein comprising a ferritin heavy chain polypeptide fused to a peptide comprising SEQ ID NO: 3, wherein said peptide is fused to the C-terminal end of the ferritin heavy chain polypeptide; and (b) at least one ferromagnetic magnetite iron oxide.

In one embodiment, this invention provides a method of imaging a biological tissue of a subject, comprising the steps of: (a) introducing (i) a nucleic acid encoding a recombinant ferritin fusion protein into cells to be imaged, or (ii) a recombinant ferritin fusion protein into cells to be imaged; and (b) imaging a biological tissue of said subject, which comprises said cells, using a MRI.

In one embodiment, this invention provides a method of determining hypoxic microenvironment state of a tumor in a subject, comprising the steps of: (a) introducing (i) a nucleic acid encoding a recombinant ferritin fusion protein into a tumor in a subject, or (ii) a recombinant ferritin fusion protein into a tumor in a subject; (b) imaging said tumor, using MRI; and (c) evaluating the image for areas of hypoxia and normoxia.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 2A shows a low magnification image of the bacteria and the magnetosome chain. FIG. 2B shows a higher magnification image of the magnetosome chain containing 10-20 cubo-octahedral crystals of magnetite. FIG. 2C shows chemical mapping of the same magnetosome chain as shown in FIG. 2B, demonstrating that the particles are made of iron. (Images 2A, 2B and 2C provided by the Faivre lab, Max Planck Institute of Colloids and Interfaces, Germany).

FIG. 4 presents the amino acid sequence of *Magnetospirillum magneticum*strain AMB-1-Mms6 protein (SEQ ID NO: 1; NCBI Accession: YP_420310.1 or BAE49760.1). The underlined sequence represents the 12 amino acid peptide sequence (SEQ ID NO: 2), derived from Mms6 protein, that is comprised in the sequence fused to the C-terminal of a ferritin polypeptide.

FIGS. 5A and 5B show SDS-PAGE fractionation results testing for mouse ferritin expression in *E. coli* Rosetta R3 cells. FIG. 5A shows the results using full length mouse ferritin heavy chain gene and FIG. 5B shows the results using the mouse ferritin-M6A fusion gene (SEQ ID NO: 7).

FIGS. 6A and 6B show biochemical characteristics of different ferritin constructs. FIG. 6A shows graphically, size exclusion chromatography of recombinant Mouse H-ferritin (SEQ ID NO: 4), Horse spleen ferritin and Mouse H-ferritin-M6A (SEQ ID NO: 7) in Superdex 200 column Protein eluted on volume corresponding to 24 mer assembly (ferritin particle complex) with molecular weight of 440 KDa similar to Horse spleen ferritin. FIG. 6B shows SDS-PAGE analysis of the corresponding Mouse H-ferritin and Mouse H-ferritin-M6A peaks.

FIGS. 7A and 7B show negatively stained (7A) and unstained (7B) horse spleen ferritin. FIGS. 7C and 7D show TEM images of the samples from negatively stained (7C) and unstained (7D) recombinant iron loaded Ferr-M6A.

FIG. 11A shows $R_2$ relaxation map of cell phantom, wherein phantoms were prepared from the cells suspended in various densities in 1% agarose. $r_2$ relaxivity, is calculated as a slope of relaxation rates $R_2$ ($1/T_2$) as a function of iron content. FIG. 11B shows a schematic representation of the samples in FIG. 11A showing the cells transfected either with HA-Ferr or HA-Ferr-M6A. The numbers indicate the number of cells in 0.26 ml of 1% agarose in PBS. Following MRI, cells were isolated and cellular iron content was determined via Inductively Coupled Plasma Mass Spectrometry (ICP-MS) (FIG. 11C). FIG. 11D presents a bar graph showing $R_2$ relaxivity, calculated as a change in $R_2$ as a function of iron content.

FIG. 12A present in vivo $R_2$ maps of axial slices through the center of C6-HA-HFn (left) and C6-HA-HFn-M6A (right) tumors FIG. 12B shows the central hypoxic region of the respective tumors, wherein the C6-HA-HFn-M6A tumors exhibits elevated MRI contrast (seen as a dark region). Corresponded $T_2$ weighted image. FIG. 12C presents a bar graph of representative $R_2$ values measured in the C6-HA-HFn (left), C6-HA-HFn-M6A (right) tumors and within the central hypoxic region of C6-HA-HFn-M6A tumor (n=3).

FIG. 18 presents a table which show different conditions in which purified ferritin-M6A and ferritin were crystallized, and images of some of the crystals formed.

Figure 1:
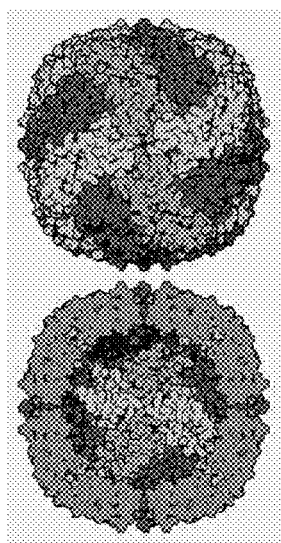
FIG. 1 is an illustration of a ferritin particle complex (Meldrum, F. C. et al., (1992) Magnetoferritin: in vitro synthesis of a novel magnetic protein, *Science* 257, 522-523).
Figure 2:
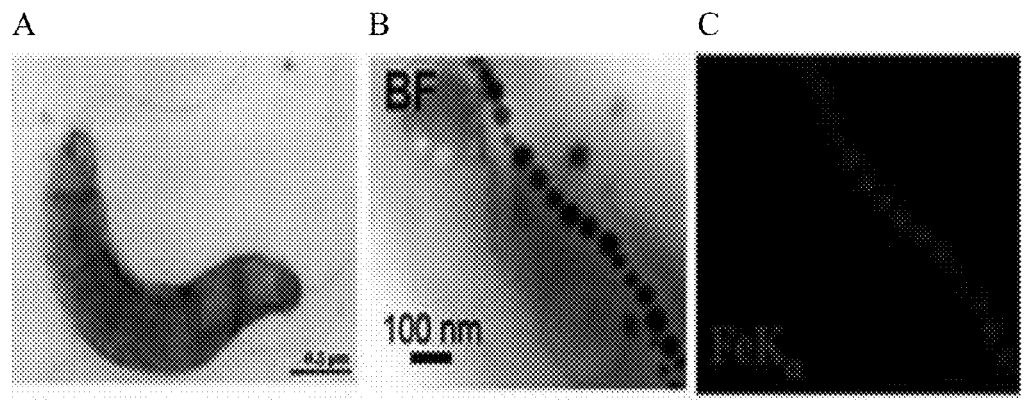
FIGS. 2A, 2B and 2C show representative transmission electron microscopy (TEM) images of *Magnetospirillum gryphiswaldense* MSR-1.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Unless defined otherwise, all technical and scientific terms herein have the same meaning as commonly understood by one of ordinary skill in the art to which this invention belongs.

The present invention is directed, in some embodiments, to a nucleic acid sequence encoding a recombinant ferritin heavy chain fusion protein, comprising a nucleic acid sequence encoding a ferritin heavy chain polypeptide fused to a peptide, wherein said peptide is fused to the C-terminal end of said ferritin heavy chain; said peptide comprising at least a portion of a Mms6 protein sequence and at least one heterologous amino acid at its N-terminal end, and methods of use thereof for non-invasive imaging of a biological sample.

I. Recombinant Ferritin-Fusion Reporter Genes and Polypeptides

In one embodiment, this invention provides a nucleic acid sequence encoding a recombinant ferritin heavy chain fusion protein, said fusion protein comprising a ferritin heavy chain polypeptide positioned N-terminal to a peptide comprising at least a portion of a Mms6 protein sequence. In one embodiment, a nucleic acid sequence encoding a recombinant ferritin heavy chain fusion protein comprises a nucleic acid sequence encoding a ferritin heavy chain polypeptide fused to a peptide, wherein said peptide is fused to the C-terminal end of said ferritin heavy chain; said peptide comprising at least a portion of a Mms6 protein sequence and at least one heterologous amino acid at its N-terminal end. In one embodiment, the peptide comprises SEQ ID NO: 3. In one embodiment, the peptide consists essentially of SEQ ID NO: 3. In one embodiment, the peptide consists of SEQ ID NO: 3.

As used herein, the terms "ferritin fusion protein", "ferritin fusion polypeptide", "ferritin heavy chain fusion polypeptide" or "ferritin heavy chain fusion protein" are used interchangeably and refer in one embodiment to any fusion protein comprising a ferritin heavy chain polypeptide fused to a portion of a Mms6 protein sequence, wherein said portion of the Mms6 protein sequence is fused at the C-terminal end of the ferritin heavy chain. In one embodiment, the portion of the Mms6 protein sequence comprises a Mms6 peptide, wherein said peptide may further comprise at least one heterologous amino acid at its N-terminal end. The term "heterologous amino acid" refers in one embodiment to an amino acid that is not found as part of the contiguous amino acid sequence of the Mms6 protein.

As used herein, the term "ferritin heavy chain polypeptide" refers in one embodiment to any of a group of diiron-carboxylate proteins characterized by the tendency to form a multimeric structure with bound iron and having a helix-bundle structure comprising an iron-coordinating Glu residue in a first helix and a Glu-X-X-His motif in a second. Certain ferritins maintain bound iron in a primarily Fe(III) state. Bacterioferritins tend to be haem proteins. In some embodiments, a ferritin heavy chain polypeptide may have an HA tag covalently bond at its N-terminal end. Vertebrate ferritins tend to be assembled from two or more subunits, and mammalian ferritins are often assembled from a heavy chain and a light chain. Many ferritins form hollow structures with an iron-rich aggregate in the interior. As used herein, the term "ferritin particle" refers to an assembly of ferritin heavy and light chains.

In one embodiment, a ferritin heavy chain of this invention may be from a mammalian source. In one embodiment, a ferritin heavy chain is a mouse ferritin heavy chain. In another embodiment, a ferritin heavy chain is a human ferritin heavy chain. In one embodiment, a human ferritin heavy chain comprises a wild-type human ferritin heavy chain.

As used herein, the term "ferritin heavy chain" may in some embodiments refer to a nucleic acid sequence encoding a polypeptide, while in other embodiments the term "ferritin heavy chain" refers to the polypeptide.

As used herein, the term "ferritin heavy chain" is used interchangeably with the terms "Ferr", "HFn", H-Ferritin" and "Ferritin".

In one embodiment, a ferritin heavy chain polypeptide of this invention is the full length, wild-type human ferritin heavy chain amino acid sequence, as known in the art. In one embodiment, a ferritin heavy chain polypeptide of this invention comprises an amino acid sequence that corresponds to that set forth in NCBI GENBANK® (GENBANK® is the NIH genetic sequence database, an annotated collection of all publicly available DNA sequences) Accession Nos. AAA52437.1 (SEQ ID NO: 10), AAA52438.1 (SEQ ID NO: 10), AAA52479.1 (SEQ ID NO: 11), AAA35833.1 (SEQ ID NO: 10), AAF89523.1 (SEQ ID NO: 10), Q9BXU8.1 (SEQ ID NO: 12), NP_002023.2 (SEQ ID NO: 10), 2CLU_A (SEQ ID NO: 13), 2IU2_A (SEQ ID NO: 14), CAP19952.1 (SEQ ID NO: 15), BAG54435.1 (SEQ ID NO: 16), BAG51427.1 (SEQ ID NO: 10) or 3AJO_A (SEQ ID NO: 17).

In one embodiment, a ferritin heavy chain polypeptide sequence is translated from a mRNA that includes a Kozak sequence at the 5'-untranslated end. In one embodiment, the Kozak sequence corresponds to SEQ ID NO: 9.

In one embodiment, a ferritin amino acid sequence lacks a leader sequence and may also include other modifications of a polypeptide such as proteolytic processing of the amino terminus (with or without a leader sequence) and/or the carboxyl terminus, cleavage of a smaller polypeptide from a larger precursor, phosphorylation, and other post-translational modifications understood by those with skill in the art.

In one embodiment, the term "amino acid" or "amino acids" is understood to include the 20 naturally occurring amino acids; those amino acids often modified post-translationally in vivo, including, for example, hydroxyproline, phosphoserine and phosphothreonine. Furthermore, the term "amino acid" may include both D- and L-amino acids.

As used herein, the term "amino acid" refers to either the D or L stereoisomer form of the amino acid, unless otherwise specifically designated. Also encompassed within the scope of this invention are equivalent proteins or equivalent peptides, e.g., having the biological activity of purified wild type ferritin. "Equivalent proteins" and "equivalent polypeptides" refer to compounds that depart from the linear sequence of the naturally occurring proteins or polypeptides, but which have amino acid substitutions that do not change it's biologically activity. These equivalents can differ from the native sequences by the replacement of one or more amino acids with related amino acids, for example, similarly charged amino acids, or the substitution or modification of side chains or functional groups.

The terms "polypeptide" and "protein", are used interchangeably and refer in one embodiment, to a polymeric form of amino acids of any length. The term includes fusion proteins, including, but not limited to, fusion proteins with a heterologous amino acid sequence, fusions with heterologous and homologous leader sequences, with or without N-terminal methionine residues; immunologically tagged proteins; and the like.

As used herein, the term "fusion protein" refers in one embodiment to an assembly of two or more protein regions, or fragments thereof, comprising for example an N-terminal ferritin heavy chain protein and a C-terminal peptide comprising at least a portion of a Mms6 protein sequence that is able to bind magnetite, wherein the C-terminal peptide is fused to the C-terminal end of the ferritin polypeptide. The C-terminal peptide, may in some embodiments, further comprise at least one heterologous amino acid at its N-terminal end that is not present in the contiguous amino acid sequence of the portion of the Mms6 protein.

Figure 15:
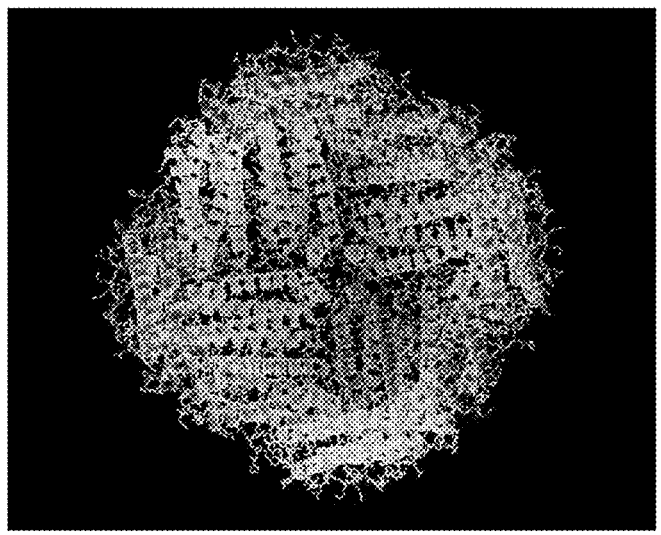
FIG. 15 presents a Ferritin-M6A crystallography structure.

An advantage of fusing a portion of a Mms6 protein to the C-terminal end of the ferritin heavy chain is that upon protein folding the peptide portion of the Mms6 protein will be buried within the inner cavity of a ferritin particle (See for example FIG. 15).

Figure 9:
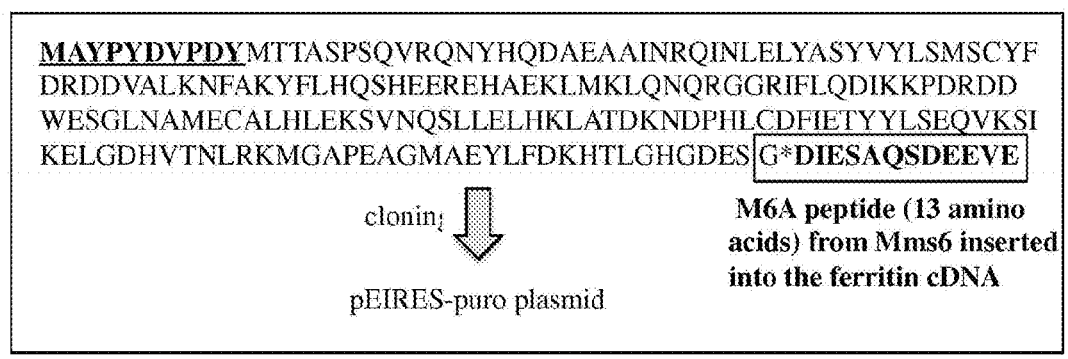
FIG. 9 presents the amino acid sequence of HA-Ferritin-M6A, wherein the underlined region represents the N-terminal HA-tag sequence and the boxed region represents the M6A peptide with an N-terminal G added (SEQ ID NO: 6). The M6A peptide sequence (SEQ ID NO: 3) represents the 12 aminoacid peptide of MMs6 (SEQ ID NO: 2) wherein an additional Glycine (G) residue has been added at the N-terminus of the peptide.

As described above, the peptide portion of a Mms6 protein may include at least one heterologous amino acid at its N-terminal end, for instance a glycine residue. In one embodiment, the peptide bound to the C-terminal end of a ferritin heavy chain comprises amino acids SEQ ID NO: 3, which includes a glycine reside followed by 12 amino acid residues found within the C-terminal portion of an Mms6 protein. (FIG. 9).

As used herein, the term "sequence" in one embodiment refers to an ordered linear sequence of nucleic acids or amino acids of a DNA or protein target sample.

The peptides or polypeptides, or the DNA sequences encoding same, may be obtained from a variety of natural or unnatural sources, such as a prokaryotic or a eukaryotic cell. In one embodiment, the source cell may be wild type, recombinant, or mutant. In another embodiment, the plurality of peptides or polypeptides may be endogenous to microorganisms, such as bacteria, yeast, or fungi, to a virus, to an animal (including mammals, invertebrates, reptiles, birds, and insects) or to a plant cell.

In another embodiment, the peptides or polypeptides may be obtained from more specific sources, such as a particular cell lysate or a tissue extract.

According to other embodiments of the present invention, recombinant gene products may be encoded by a polynucleotide having a modified nucleotide sequence, as compared to a corresponding natural polynucleotide.

In one embodiment, a ferritin heavy chain nucleic acid sequence corresponds to a mRNA sequence coding for the full-length ferritin heavy chain polypeptide. In one embodiment, a ferritin heavy chain of this invention is a full length, wild-type human ferritin heavy chain nucleic acid sequence, as known in the art. In one embodiment, a ferritin heavy chain nucleic acid sequence of this invention comprises a nucleotide sequence that corresponds to that set forth in NCBI GENBANK® (GENBANK® is the NIH genetic sequence database, an annotated collection of all publicly available DNA sequences) Accession Nos. NM_002032.2 (SEQ ID NO: 18), M15383.1 (SEQ ID NO: 19), L20941.1 (SEQ ID NO: 20), M97164.1 (SEQ ID NO: 21), M11146.1 (SEQ ID NO: 22), AF088851.1 (SEQ ID NO: 23), AK127090.1 (SEQ ID NO: 24), AK054816.1 (SEQ ID NO: 25) or AK095899.1 (SEQ ID NO: 26).

In one embodiment, a ferritin heavy chain nucleic acid sequence includes upstream untranslated regions. In one embodiment, an upstream untranslated region of this invention corresponds to that set forth in NCBI GENBANK® (GENBANK® is the NIH genetic sequence database, an annotated collection of all publicly available DNA sequences) Accession No. D28463.1. In one embodiment, an upstream untranslated region of this invention corresponds to a Kozak sequence (SEQ ID NO: 9).

As used herein, the term "nucleic acid" refers to polynucleotide or to oligonucleotides such as deoxyribonucleic acid (DNA), and, where appropriate, ribonucleic acid (RNA) or mimetic thereof. The term should also be understood to include, as equivalents, analogs of RNA or DNA made from nucleotide analogs, and, as applicable to the embodiment being described, single (sense or antisense) and double-stranded polynucleotide. This term includes oligonucleotides composed of naturally occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

In one embodiment, the term "nucleic acid" or "oligonucleotide" refers to a molecule, which may include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also refers to sequences that include any of the known base analogs of DNA and RNA.

The nucleic acids can be produced by any synthetic or recombinant process, which are well known in the art. Nucleic acids can further be modified to alter biophysical or biological properties by means of techniques known in the art. For example, the nucleic acid can be modified to increase its stability against nucleases (e.g., "end-capping"), or to modify its solubility, or binding affinity to complementary sequences. These nucleic acids may comprise the vector, the expression cassette, the promoter sequence, the gene of interest, or any combination thereof. In another embodiment, its lipophilicity may be modified, which, in turn, will reflect changes in the systems employed for its delivery, and in one embodiment, may further be influenced by whether such sequences are desired for retention within, or permeation through the skin, or any of its layers. Such considerations may influence any compound used in this invention, in the methods and systems described.

In one embodiment, DNA can be synthesized chemically from the four nucleotides in whole or in part by methods known in the art. Such methods include those described in Caruthers (1985; Science 230:281-285). DNA can also be synthesized by preparing overlapping double-stranded oligonucleotides, filling in the gaps, and ligating the ends together (see, generally, Sambrook et al. (1989; Molecular Cloning—A Laboratory Manual, 2nd Edition. Cold Spring Habour Laboratory Press, New York)). In another embodiment, inactivating mutations may be prepared from wild-type DNA by site-directed mutagenesis (see, for example, Zoller et al. (1982; DNA. 1984 December; 3(6):479-88); Zoller (1983); and Zoller (1984; DNA. 1984 December; 3(6):479-88); McPherson (1991; Directed Mutagenesis: A Practical Approach. Oxford University Press, NY)). The DNA obtained can be amplified by methods known in the art. One suitable method is the polymerase chain reaction (PCR) method described in Saiki et al. (1988; Science. 1988 Jan. 29; 239(4839):487-491), Mullis et al., U.S. Pat. No. 4,683,195, and Sambrook et al. (1989).

Methods for modifying nucleic acids to achieve specific purposes are disclosed in the art, for example, in Sambrook et al. (1989). Moreover, the nucleic acid sequences of the invention can include one or more portions of nucleotide sequence that are non-coding for the protein of interest. Variations in DNA sequences, which are caused by point mutations or by induced modifications (including insertion, deletion, and substitution) to enhance the activity, half-life or production of the polypeptides encoded thereby, are also encompassed in the invention.

In one embodiment, a nucleic acid molecule encoding a ferritin heavy chain polypeptide encodes an amino acid sequence that is at least about 95% identical to a wild-type amino acid sequence. In another embodiment, a nucleic acid molecule encoding a ferritin heavy chain polypeptide encodes an amino acid sequence that is at least about 96% identical to a wild-type amino acid sequence. In yet another embodiment, a nucleic acid molecule encoding a ferritin heavy chain polypeptide encodes an amino acid sequence that is at least about 97% identical to a wild-type amino acid sequence. In still another embodiment, a nucleic acid molecule encoding a ferritin heavy chain polypeptide encodes an amino acid sequence that is at least about 98% identical to a wild-type amino acid sequence. In a further embodiment, a nucleic acid molecule encoding a ferritin heavy chain polypeptide encodes an amino acid sequence that is at least about 99% identical to a wild-type amino acid sequence.

In one embodiment, a nucleic acid molecule encoding a ferritin heavy chain comprises a nucleotide sequence that is at least about 95% identical to a wild-type nucleotide sequence. In another embodiment, a nucleic acid molecule encoding a ferritin heavy chain comprises a nucleotide sequence that is at least about 96% identical to a wild-type nucleotide sequence. In yet another embodiment, a nucleic acid molecule encoding a ferritin heavy chain comprises a nucleotide sequence that is at least about 97% identical to a wild-type nucleotide sequence. In still another embodiment, a nucleic acid molecule encoding a ferritin heavy chain comprises a nucleotide sequence that is at least about 98% identical to a wild-type nucleotide sequence. In a further embodiment, a nucleic acid molecule encoding a ferritin heavy chain comprises a nucleotide sequence that is at least about 99% identical to a wild-type nucleotide sequence.

In one embodiment, this invention provide a fusion protein encoded by a nucleic acid construct that causes the expression of an mRNA comprising at least two coding regions, for example, at least two open reading frames. In other words, two or more open reading frames may be organized into a "translational fusion" such that both open reading frames will be expressed as part of a single mRNA and then give rise, as specified by the host cell, to a single polypeptide. The fused polypeptides in a "translational fusion" tend to experience similar transcriptional, translational and post-translational regulation.

As will be appreciated by one skilled in the art, a fragment or derivative of a nucleic acid sequence or gene that encodes for a protein or peptide can still function in the same manner as the entire wild type gene or sequence. Likewise, forms of nucleic acid sequences can have variations as compared to wild type sequences, nevertheless encoding the protein or peptide of interest, or fragments thereof, retaining wild type function exhibiting the same biological effect, despite these variations. Each of these represents a separate embodiment of this present invention.

In one embodiment, the term "peptide" refers to native peptides (either synthetically synthesized peptides or recombinant peptides). In one embodiment, a Mms6 peptide comprises amino acid sequence SEQ ID NO: 2. In another embodiment, a peptide of this invention comprises amino acid sequence SEQ ID NO: 3.

The term "portion" as used herein, refers in one embodiment to a physically contiguous portion of the primary structure of a biomolecule. In the case of proteins, a portion is defined by a contiguous portion of the amino acid sequence of that protein and refers in one embodiment, to at least 3-5 amino acids, in another embodiment to at least 8-10 amino acids, in a further embodiment to at least 11-15 amino acids, in yet another embodiment to 12 amino acids, in a further embodiment to greater than 12 amino acids. In one embodiment, a portion of the Mms6 protein sequence comprises SEQ ID NO: 2.

In the case of oligonucleotides, a portion is defined by a contiguous portion of the nucleic acid sequence of that oligonucleotide and refers in one embodiment to at least 9-15 nucleotides, in another embodiment to at least 18-30 nucleotides, in yet another embodiment to at least 33-45 nucleotides, in still another embodiment to 36 nucleotides, in a further embodiment to greater than 45 nucleotides.

In some embodiments, portions of biomolecules have a biological activity. In the context of the present invention, a portion of a Mms6 protein does not comprise the entire Mms6 polypeptide sequence set forth in SEQ ID NO:1 (FIG. 4). In one embodiment, the biological activity is binding magnetite. In one embodiment, the biological activity is conversion of ferrihydrite into magnetite. In one embodiment, the biological activity is conversion of Fe(II) to ferromagnetic magnetite iron oxide.

The invention further encompasses peptides having a desired function, for example binding magnetite, wherein the peptide further comprises at least one heterologous amino acid at its N-terminal end, which is not present as part of the contiguous Mms6 protein sequence. Addition of an at least one amino acid residue at the N-terminal end of the peptide assist in proper three-dimensional polypeptide folding of the full-length fusion protein. In one embodiment, addition of at least one heterologous amino acid residue at the N-terminal end of a peptide of this invention provides for or assists in proper tertiary structure of a fusion protein of this invention. The tertiary structure of a polypeptide may influence oligomerization characteristics of a ferritin fusion protein and therefore affect assembly of fusion proteins into a symmetric homo-oligomeric sphere, for example, a ferritin particle. The tertiary structure of a ferritin-Mms6 peptide fusion protein may also influence binding of iron oxides to the fusion protein and/or within the core of a ferritin particle. Additional, the tertiary structure of a ferritin-Mms6 peptide fusion protein may influence conversion of ferrihydrite into magnetite.

As used herein, the term "ferritin-Mms6 peptide fusion protein refers in one embodiment to a fusion protein comprising a ferritin heavy chain polypeptide fused to a peptide, wherein said peptide is fused to the C-terminal end of said ferritin heavy chain; and said peptide comprises at least a portion of a Mms6 protein sequence and at least one heterologous amino acid at its N-terminal end. In one embodiment, the peptide comprises SEQ ID NO: 3.

In one embodiment, a fusion protein of this invention is incorporated into a ferritin particle. In one embodiment, a fusion protein incorporated into a ferritin particle forms a hollow-sphere wherein the peptide sequence comprising a portion of the Mms6 protein sequence is incorporated within the hollow core of the ferritin particle. In one embodiment, the peptide sequence comprising a portion of the Mms6 protein sequence comprises SEQ ID NO: 2.

In one embodiment, a peptide sequence comprising a portion of the Mms6 protein sequence further comprises at least one heterologous amino acid at the N-terminal end of the peptide. In one embodiment a peptide of this invention may further comprise a glycine residue at its N-terminal end. In one embodiment, a peptide sequence comprises SEQ ID NO: 3. In another embodiment, a peptide of this invention comprises at least one of any of the known, naturally occurring amino acids at the N-terminal end of the peptide comprising a portion of the Mms6 protein.

In one embodiment, a Mms6 peptide further comprises at least one amino acid at its N-terminus which is not present in the Mms6 protein sequence, i.e., a heterologous amino acid. In one embodiment, a peptide of this invention comprises amino acid sequence SEQ ID NO: 3. In one embodiment, the term "M6A peptide" refers to amino acid SEQ ID NO: 3. In one embodiment, a peptide of this invention consists of amino acid sequence SEQ ID NO: 3. In one embodiment, a peptide comprising amino acid sequence SEQ ID NO: 3 is fused to the C-terminal end of a ferritin heavy chain. In another embodiment, a peptide consisting of amino acid sequence SEQ ID NO: 3 is fused to the C-terminal end of a ferritin heavy chain.

In one embodiment, a fusion protein of this invention may be termed "ferritin-M6A", ferritin:M6A", "Ferritin-Mms6", "Ferr-M6A", "H-Ferritin-M6a", "HA-Ferritin-M6A", "HFn-M6A" or "HA-HFn-M6A".

In one embodiment, a ferritin fusion protein, for example, ferritin-M6A, is isolated and reconstituted with Fe(II) to form a magnetic mineral, magnetite. In one embodiment, a ferritin fusion protein, for example, ferritin-M6A, is isolated and reconstituted with Fe(II) to form a ferromagnetic magnetite iron oxide.

In some embodiments, a ferritin fusion protein may comprise additional heterologous amino acid sequences, for instance an immunologically tag resulting in an immunologically tagged protein. Heterologous amino acid sequences may comprise HIS, tags, HA tags or any tag as is known in the art. In one embodiment, the tag sequence is contiguous with the N-terminal end of the fusion protein. In some embodiments, a nucleic acid sequence of this invention encodes a ferritin fusion protein with an immunological tag.

In one embodiment, a ferritin fusion protein of this invention may be a contrast agent useful for providing increased contrast in an image of a biological sample. For instance, in one embodiment a ferritin fusion protein of this invention may be used as an MRI contrast agent.

As used herein, the term "contrast agent" refers in one embodiment to a molecule that generates a contrasting effect in vitro or in vivo, whether the effect is direct or indirect or both. As used herein, the term "contrast agent" is used interchangeably with "contrast protein", "contrast polypeptide", "reporter agent", "reporter gene", "reporter polypeptide", "contrast enhancement agent" or reporter protein". In one embodiment, a contrast agent is a nucleic acid encoding a ferritin fusion protein, wherein the effect may be considered indirect. That is upon expression of the nucleic acid encoding the ferritin fusion protein, the expressed protein comprises the contrast agent. In one embodiment, a contrast agent is a ferritin fusion protein, as described below, wherein the effect may be considered direct.

In one embodiment a fusion protein of this invention comprises a ferritin heavy chain polypeptide positioned N-terminal to a peptide comprising at least a portion of a Mms6 protein sequence. In one embodiment, the peptide comprises SEQ ID NO: 2. In another embodiment, a peptide further comprises at least one amino acid at its N-terminus which is not present in the Mms6 protein sequence. In one embodiment a peptide comprising at least one amino acid at its N-terminus not present in the Mms6 protein comprises SEQ ID NO: 3. In another embodiment, a peptide comprising at least one amino acid at its N-terminus not present in the Mms6 protein consists essentially of SEQ ID NO: 3. In one embodiment, the amino acid sequence of SEQ ID NO: 3 is fused to the C-terminal of said ferritin heavy chain. In one embodiment, there is a linker between the ferritin heavy chain of at least one amino acid. In another embodiment, there is no linker between the ferritin heavy chain and SEQ ID NO: 3. In some embodiments, a ferritin heavy chain polypeptide is a human ferritin heavy chain polypeptide.

In one embodiment, a recombinant ferritin heavy chain fusion protein of this invention is isolated. As used herein, the term "isolated" means a polypeptide that is substantially free of, nucleic acids, lipids, carbohydrates or other materials with which they can be associated, such association being either in cellular material or in a synthesis medium, and substantially free from other undesired peptides and polypeptides (See for example FIGS. 3, 5A, 5B, 6A, 6B and 10B).

In some embodiment, the presence of a "tag" peptide sequence at the N-terminus or C-terminus of a ferritin fusion protein is used as a means for purification or immunodetection purposes. A ferritin fusion protein may be isolated by any means known in the art. For example, using methods that include column chromatography (size exclusion, immuno, Ni-binding, high-performance liquid chromatography (HPLC), low-pressure liquid chromatography (LPLC), fast-protein liquid chromatograph (FPLC)).

In one embodiment, a nucleic acid of this invention is comprised in a vector. In some embodiments, the vector of and for use in the methods of the present invention comprises a nucleic acid sequence operably linked to one or more regulatory sequences, wherein said nucleic acid sequence encodes a ferritin fusion protein of this invention as described above. In another embodiment, the vector consists essentially of such a nucleic acid sequence, and in another embodiment, the vector consists of such a nucleic acid sequence.

In one embodiment, a vector is a mammalian expression vector, wherein a gene product may be expressed. In one embodiment, the term "gene" refers to a nucleic acid fragment that is capable of being expressed as a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. A "translational fusion" gene, comprises a nucleic acid construct that causes the expression of an mRNA comprising at least two coding regions, for example, at least two open reading frames. For example, in one embodiment, gene product expression includes expression of any ferritin fusion gene as described herein. In another embodiment, a gene product expressed is a ferritin fusion gene. In yet another embodiment, a gene product expressed is a ferritin-M6A fusion gene. The term "ferritin-M6A" refers in one embodiment to a heavy chain ferritin polypeptide fused to SEQ ID NO: 3, wherein said peptide is fused to the C-terminal end of the heavy chain ferritin polypeptide. In one embodiment, the heavy chain ferritin is a mammalian ferritin. In one embodiment, the heavy chain ferritin is a mouse ferritin. In one embodiment, the heavy chain ferritin is a human ferritin.

In one embodiment, a ferritin fusion protein may be expressed. In one embodiment, a ferritin fusion protein of this invention is over-expressed. In one embodiment, the expressed gene product is a human ferritin-MA6 polypeptide.

As used herein, the term "expression" generally refers to the cellular processes by which a biologically active peptide or polypeptide is produced from RNA.

Any one of a number of different vectors can be used, such as viral vectors, plasmid vectors, linear DNA, etc., as known in the art, to introduce an exogenous nucleic acid fragment encoding a therapeutic agent into target cells and/or tissue. These vectors can be inserted, for example, using infection, transduction, transfection, calcium-phosphate mediated transfection, DEAE-dextran mediated transfection, electroporation, liposome-mediated transfection, biolistic gene delivery, liposomal gene delivery using fusogenic and anionic liposomes (which are an alternative to the use of cationic liposomes), direct injection, receptor-mediated uptake, magnetoporation, ultrasound, or any combination thereof, as well as other techniques known in the art (for further detail see, for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals). The polynucleotide segments encoding sequences of interest can be ligated into an expression vector system suitable for transducing mammalian cells and for directing the expression of recombinant products within the transduced cells. The introduction of the exogenous nucleic acid sequence is accomplished by introducing the vector into the vicinity of a cell. Alternatively, introduction of the exogenous nucleic acid sequence comprised in a vector is accomplished by administrating a vector to a subject. Once the exogenous nucleic acid sequence has been incorporated into the cells using any of the techniques described above or known in the art, the production and/or the secretion rate of the fusion protein encoded by the nucleic acid sequence can be quantified.

In one embodiment, a vector is a non-immunogenic gene transfer agent such as a nonviral vector (e.g. DNA plasmids or minicircle DNA), a "gutless" viral vector i.e. without endogenous genes (which in one embodiment, is due to a deletion, while in another embodiment, due to an insertion, substitution or deletion in a gene that prevents viral gene expression), a helper-dependent adenovirus vector, or adeno associated virus AAV (which in one embodiment is single stranded and in another embodiment, double stranded). In another embodiment, a ferritin fusion gene is so chosen such that recombinant gene expression results in lack of toxicity or immune-mediated rejection of the gene product by a subject. In one embodiment, the vector is virally derived, and in another embodiment, the vector is a plasmid. In one embodiment, the virally-derived vector is derived from adenovirus, which in one embodiment, is helper-dependent adenovirus, while in another embodiment, the virally-derived vector is derived from adenovirus-associated vector, as is described herein below.

In one embodiment, the term "vector" or "expression vector" refers to a carrier molecule into which a nucleic acid sequence can be inserted for introduction into a cell where it can be expressed. In one embodiment, the nucleic acid molecules are transcribed into RNA, which in some cases are then translated into a protein, polypeptide, or peptide. In one embodiment, expression vectors can contain a variety of "control sequences" which refer to nucleic acid sequences necessary for the transcription and possibly translation of an operably linked coding sequence in a particular host cell. In another embodiment, a vector further includes an origin of replication. As used herein, the term "control sequence" may also be referred to herein as a "regulatory sequence". In one embodiment the vector may be a shuttle vector, which in one embodiment can propagate both in prokaryotic and eukaryotic cells, or in another embodiment, the vector may be constructed to facilitate its integration within the genome of a cell of choice. The vector, in other embodiments may be, for example, a plasmid, a bacmid, a phagemid, a cosmid, a phage, a virus or an artificial chromosome. In one embodiment, the vector is a viral vector, which in one embodiment may be a bacteriophage, mammalian virus, or plant virus.

In one embodiment, the viral vector is an adenoviral vector. In another embodiment, the adenovirus may be of any known serotype or subgroup.

Advantages of using an adenoviral vector as a gene transfer vector are: its mid-sized genome, ease of manipulation, high titer, wide target-cell range and high infectivity. Both ends of the adenoviral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off. The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNAs issued from this promoter possess a 5'-tripartite leader (TPL) sequence which makes them preferred mRNAs for translation.

In another embodiment, the adenoviral vector is a helper-dependent adenoviral vector, which in another embodiment, is synonymous with gutless, gutted, mini, fully deleted, high-capacity, Δ or pseudo adenovirus, and which in another embodiment are deleted of all viral coding sequences except for sequences supporting DNA replication, which in one embodiment, comprise the adenovirus inverted terminal repeats and packaging sequence (Ψ). In another embodiment, helper-dependent adenoviruses express no viral genes In one embodiment, a helper-dependent adenoviral vector comprises only the cis-acting elements of the adenovirus required to replicate and package the vector DNA. In one embodiment, a helper-dependent adenoviral vector comprises approximately 500 bp of wild-type adenovirus sequence. In another embodiment, the adenoviral vector additionally comprises stuffer DNA to meet the minimum requirement for a genome size of 27.7 kb, which in one embodiment is required for efficient packaging into the adenovirus capsid. In one embodiment, non-coding mammalian DNA, with minimal repeat sequences, is used as stuffer DNA. In another embodiment, stuffer DNA comprises non-mammalian DNA, which in one embodiment, is HPRT and/or C346 cosmid sequences. In one embodiment, the HDAd vector is a non-replicating vector.

In one embodiment, helper-dependent adenoviruses display high-efficiency in vivo transduction, high-level transgene expression, are able to maintain long-term transgene expression, in one embodiment, by avoiding chronic toxicity due to residual expression of viral proteins, or a combination thereof. In another embodiment, helper-dependent adenoviruses have high titer production, efficient infection of a broad range of cell types, the ability to infect dividing and non-dividing cells, or a combination thereof. In still another embodiment, a helper-dependent adenovirus for use in the methods of the instant invention does not induce high cytotoxic T cell levels (as may be measured in one embodiment by positive CD8 staining, as is known in the art), and, in another embodiment, does not induce high helper T cell levels (as may be measured in one embodiment by positive CD4 stain, as is known in the art).

In another embodiment, helper-dependent adenoviruses have a lower risk of germ line transmission and insertional mutagenesis that may cause oncogenic transformation, because the vector genome does not integrate into the host cell chromosomes. In one embodiment, the cloning capacity of helper-dependent adenoviruses is very large (in one embodiment, approximately 37 kb, in another embodiment, approximately 36 kb), allowing for the delivery of whole genomic loci, multiple transgenes, and large cis-acting elements to enhance, prolong, and regulate transgene expression.

In one embodiment, the helper-dependent adenovirus system for use with the compositions and in the methods of the present invention is similar to that described in Palmer and Ng, 2003 (Mol Ther 8:846) and in Palmer and Ng, 2004 (Mol Ther 10:792), which are hereby incorporated herein by reference in their entirety. In one embodiment, there is a stuffer sequence inserted into the E3 region of the helper virus component of the helper-dependent adenovirus system to minimize recombination between the helper adenovirus and the helper-dependent adenovirus to produce replication competent adenovirus.

In another embodiment, the adenoviral vector is E1-deleted, while in another embodiment, the adenoviral vector additionally comprises deletions for E2, E3, E4, or a combination thereof.

In another embodiment, the viral vector is an adeno-associated viral vector (AAV). In one embodiment, AAV is a parvovirus, discovered as a contamination of adenoviral stocks. It is a ubiquitous virus (antibodies are present in 85% of the US human population) that has not been linked to any disease. It is also classified as a dependovirus, because its replication is dependent on the presence of a helper virus, such as adenovirus. At least nine serotypes have been isolated, of which AAV-2 is the best characterized. AAV may have single-stranded linear DNA that is encapsidated into capsid proteins VP1, VP2 and VP3 to form an icosahedral virion of 20 to 24 nm in diameter.

In one embodiment, the AAV DNA is approximately 4.7 kilobases long. In one embodiment, it contains two open reading frames and is flanked by two ITRs. There are two major genes in the AAV genome: rep and cap. The rep gene codes for proteins responsible for viral replications, whereas cap codes for capsid protein VP1-3. Each ITR forms a T-shaped hairpin structure. These terminal repeats are the only essential cis components of the AAV for chromosomal integration. Therefore, in one embodiment, the AAV can be used as a vector with all viral coding sequences removed and replaced by the cassette of genes for delivery. In one embodiment, the AAV is rep negative.

In one embodiment, when using recombinant AAV (rAAV) as an expression vector, the vector comprises the 145-bp ITRs, which are only 6% of the AAV genome, which in one embodiment, leaves space in the vector to assemble a 4.5-kb DNA insertion.

In one embodiment, AAV is safe in that it is not considered pathogenic nor is it associated with any disease. The removal of viral coding sequences minimizes immune reactions to viral gene expression, and therefore, rAAV evokes only a minimal inflammatory response, if any. In another embodiment, AAV vector is double-stranded, while in another embodiment, AAV vector is self-complementary, which in one embodiment, bypasses the requirement of viral second-strand DNA synthesis, which in one embodiment, results in early transgene expression.

In another embodiment, the viral vector is a retroviral vector. Retroviruses are a group of single-stranded RNA viruses characterized by an ability to convert their RNA to double-stranded DNA in infected cells by a process of reverse-transcription. The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome.

In order to construct a retroviral vector in one embodiment, a nucleic acid encoding one or more oligonucleotide or polynucleotide sequences of interest is inserted into the viral genome in the place of certain viral sequences to produce a virus that is replication-defective. In order to produce virions, a packaging cell line containing the gag, pol, and env genes but without the LTR and packaging components is constructed. When a recombinant plasmid containing a cDNA, together with the retroviral LTR and packaging sequences is introduced into this cell line (by calcium phosphate precipitation, for example), the packaging sequence allows the RNA transcript of the recombinant plasmid to be packaged into viral particles, which are then secreted into the culture media. The media containing the recombinant retroviruses is then collected, optionally concentrated, and used for gene transfer. Retroviral vectors are able to infect a broad variety of cell types. However, integration and stable expression require the division of host cells.

In other embodiments, the viral vector is derived from a virus such as vaccinia virus, lentivirus, polio virus, hepatitis virus, papilloma virus, cytomegalovirus, simian virus, or herpes simplex virus.

In one embodiment, a vector of this invention comprises a pEIRES plasmid vector (Hobbs S, Jitrapakdee S, Wallace J C. Biochem Biophys Res Commun 1998 252:368-72. Development of a bicistronic vector driven by the human polypeptide chain elongation factor 1alpha promoter for creation of stable mammalian cell lines that express very high levels of recombinant proteins.). The pEIRES vector is a mammalian expression vector that allows for simultaneous high level expression of two genes of interest from the same bicistronic mRNA transcript, for example as presented here, expression of a ferritin heavy chain gene and the puromycin resistance gene. In addition, the pEIRES vector contains the strong E1 human polypeptide chain elongation factor 1α promoter.

In certain embodiments of the invention, the vector comprising a nucleic acid sequence may comprise naked recombinant DNA or plasmids. Transfer of the construct may be performed by any method which physically or chemically permeabilizes the cell membrane. In one embodiment, the vector is a mini-circle DNA, which in one embodiment, is a supercoiled DNA molecule for non-viral gene transfer, which has neither a bacterial origin of replication nor an antibiotic resistance marker. In another embodiment, mini-circle DNA comprises no bacterial control regions from gene delivery vectors during the process of plasmid production. They are thus smaller and potentially safer than other plasmids used in gene therapy. In one embodiment, mini-circle DNA produce high yield, are simple to purify, and provide robust and persistent transgene expression.

Construction of vectors using standard recombinant techniques is well known in the art (see, for example, Maniatis, et al., Molecular Cloning, A Laboratory Manual (Cold Spring Harbor, 1990) and Ausubel, et al., 1994, Current Protocols in Molecular Biology (John Wiley & Sons, 1996), both incorporated herein by reference).

In one embodiment, a vector comprising a nucleic acid encoding a ferritin fusion protein of the instant invention, for example a ferritin-M6A polypeptide, is introduced into a prokaryotic or eukaryotic host cell. There are a number of techniques known in the art for introducing cassettes and/or vectors into cells, for affecting the methods of the present invention, such as, but not limited to: direct DNA uptake techniques, and virus, plasmid, linear DNA or liposome mediated transduction, receptor-mediated uptake and magnetoporation methods employing calcium-phosphate mediated and DEAE-dextran mediated methods of introduction, electroporation or liposome-mediated transfection, (for further detail see, for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals).

In one embodiment, bombardment with nucleic acid coated particles may be a method for transferring a naked DNA expression construct into cells. This method depends on the ability to accelerate DNA-coated micro-projectiles to a high velocity allowing them to pierce cell membranes and enter cells without killing them. Several devices for accelerating small particles have been developed. One such device relies on a high voltage discharge to generate an electrical current, which in turn provides the motive force. The micro-projectiles used have comprised biologically inert or biocompatible substances such as tungsten or gold beads. It is to be understood that any of these methods may be utilized for introduction of the desired sequences into cells, and cells thereby produced are to be considered as part of this invention, as is their use for effecting the methods of this invention.

In certain embodiments, a ferritin fusion protein of this invention, for example ferritin-M6A, may be a MRI contrast agent useful for providing increased contrast in an image of a biological sample. In one embodiment, a ferritin-M6A contrast agent comprises: (a) an isolated, recombinant fusion protein comprising a ferritin heavy chain polypeptide fused to a peptide comprising SEQ ID NO: 3, wherein said peptide is fused to the C-terminal end of the ferritin heavy chain polypeptide; and (b) at least one ferromagnetic magnetite iron oxide. In one embodiment, a ferritin-M6A contrast agent comprises a human ferritin heavy chain.

II. Non-Invasive Imaging

A nucleic acid encoding a ferritin fusion protein, as described above, may be used in any of the methods described below. Further, a ferritin fusion protein, as described above may be used in any of the methods described below.

In one embodiment, this invention provides a method of imaging a biological tissue of a subject, comprising the steps of: (a) introducing (i) a nucleic acid encoding a recombinant ferritin fusion protein into cells to be imaged, or (ii) a recombinant ferritin fusion protein into cells to be imaged; and imaging a biological tissue of said subject, which comprises said cells, using a MRI Standard MRI equipment, conditions and techniques can be used to generate images; appropriate equipment, conditions and techniques can be determined in the course of experimental design.

As used herein, the term Magnetic Resonance Imaging ("MRI") refers in one embodiment to a non-invasive diagnostic and research procedure that uses a large, high-strength magnet and radio-frequency signals to produce images. MRI is able to generate structural information in three dimensions in a relatively short period of time.

In one embodiment, use of a ferritin fusion protein of this invention enhances contrast of a MRI image. MRI may be performed in vitro on protein solutions, in vitro on cells suspensions and/or in vivo on a biological tissue sample of a subject.

A purified ferritin fusion protein solutions may be reconstituted with an Fe(II) solution. Further, an isolated protein solution comprising a ferritin fusion protein may be reconstituted with at least one ferromagnetic magnetite iron oxide. A cell suspension comprising a nucleic acid encoding and expressing a ferritin fusion protein may include addition of ferric citrate. Further, a subject may be on a high iron diet. In each case, inclusion of Fe(II), a ferromagnetic magnetite iron oxide, ferric citrate, or a high iron diet, may in certain circumstances lead to enhanced contrast of a MRI image.

As used herein, the term "purified" is interchangeable with the term "isolated".

In one embodiment, a contrast enhancement agent, for instance a nucleic acid encoding a ferritin fusion protein of this invention can be introduced into a biological structure comprised in a subject. In another embodiment, a contrast enhancement agent, for instance a ferritin fusion protein of this invention, can be introduced into a biological structure comprised in a subject.

The mode of administration of a contrast enhancement agent of the invention to a sample, for example cells, or subject can determine the sites and/or cells in the organism to which an agent will be delivered. The contrast enhancement agents of the present invention will generally be administered in admixture with a pharmaceutical diluent selected with regard to the intended route of administration and standard pharmaceutical practice. The preparations can be injected into a subject parenterally, for example, intra-arterially or intravenously. For parenteral administration, a preparation can be used, e.g., in the form of a sterile, aqueous solution; such a solution can contain other solutes, including, but not limited to, salts or glucose in quantities that will make the solution isotonic.

In one embodiment, a contrast enhancement agent is parenterally administered. In another embodiment, a contrast enhancement agent can be injected directly into a tumor. In one embodiment, the preparation will be injected in accordance with the above guidelines. In yet another embodiment, a contrast enhancement agent may be targeted to a tissue, including tumor tissue, by any means known in the art. In a further embodiment, cells are transfected with a contrast enhancement agent of this invention, following which said cells are introduced into a subject. In one embodiment, a contrast enhancement agent of this invention comprises a nucleic acid encoding a ferritin fusion protein as described above. In another embodiment, a contrast enhancement agent of this invention comprises a ferritin fusion protein as described above.

When a contrast enhancement agent of the present invention is administered to a human subject, the prescribing physician will ultimately determine the appropriate dosage for a given human subject, and this can be expected to vary according to the weight, age and response of the individual as well as the nature and severity of the patient's condition.

In one embodiment, a subject of this invention is a mammalian subject. In one embodiment, a subject of this invention is a human subject.

In one embodiment, in vitro reconstitution of an isolated ferritin fusion protein, for example ferritin-M6A, with an Fe(II) solution, enhances MRI contrast. In one embodiment, in vitro addition of ferric citrate to a cell-suspension comprising cells transfected with a ferritin fusion protein, for example Ferr-M6A, enhances MRI contrast. In one embodiment, in vivo MRI imaging of a biological tissue of a subject on a high iron diet, wherein a nucleic acid encoding a ferritin fusion protein for example Ferr-M6A, has been introduced into said subject, enhances MRI contrast of the tissue being evaluated. In another embodiment, in vivo MRI imaging of tissue of a subject on a high iron diet, wherein a ferritin fusion protein for example Ferr-M6A, has been introduced into said subject, enhances MRI contrast of the tissue being evaluated.

In one embodiment, a biological sample comprises isolated cells, at least a portion of which are expressing a ferritin fusion protein of this invention. In another embodiment, a biological sample comprises cells located within any tissue of a subject's body, wherein at least a portion of the cells are expressing a ferritin fusion protein of this invention. In yet another embodiment, a biological sample comprises any biological tissue of a subject's body, wherein at least a portion of the cells within the tissue are expressing a ferritin fusion protein of this invention. In still another embodiment, a biological sample comprises tumor tissue, wherein at least a portion of the cells within the tumor are expressing a ferritin fusion protein of this invention. In one embodiment, a tumor may be located within a subject's body. In another embodiment, a tumor or a portion thereof, may have been surgically removed from a subject's body prior to MRI imaging. In one embodiment, a biological sample is comprised in a subject.

In one embodiment, a MRI method of this invention scans a biological sample, wherein the scanning may be in vitro or in vivo. In one embodiment, the biological sample is cells and said scanning is in vitro.

In some embodiment, methods of this invention comprise use of any nucleic acid sequence encoding a ferritin fusion protein as described above. In some embodiment, methods of this invention comprise use of any ferritin fusion polypeptide as described above. In certain embodiments, a method of this invention comprises a nucleic acid sequence encoding a ferritin fusion protein, or the ferritin fusion protein itself, wherein said ferritin fusion protein comprises a ferritin heavy chain polypeptide fused to a M6A peptide comprising SEQ ID NO: 3, wherein said M6A peptide is fused to the C-terminal end of at the ferritin heavy chain polypeptide.

In one embodiment, cells transfected with a nucleic acid sequence encoding a ferritin fusion protein of this invention are used to inoculate a subject. In one embodiment, a method of this invention comprises a subject on a high iron diet.

In one embodiment, the presence of a recombinant ferritin fusion polypeptide enhances image contrast in a method of this invention. In one embodiment, the presence of a nucleic acid encoding a recombinant ferritin fusion polypeptide enhances image contrast in a method of this invention.

In one embodiment, a method of this invention may be used for evaluating medical therapies including tracking cell location(s) in vivo following a cellular based therapy, stem cell therapy, bone marrow transplantation, gene therapy and immune cell therapy.

In one embodiment, a method of this invention may be used for evaluating tissue microenvironment. In one embodiment, evaluating tissue microenvironment comprises identifying normoxic and hypoxic microenvironments in said tissue. In one embodiment, tissue microenvironment comprises microenvironment of tumor tissue.

In one embodiment, the present invention presents a method of determining hypoxic microenvironment state of a tumor in a subject, comprising the steps of: (a) introducing a nucleic acid encoding a recombinant ferritin fusion protein into a tumor in a subject; (b) imaging said tumor, using a MRI technique; and (c) evaluating the image for areas of hypoxia and normoxia. The importance of evaluating areas of hypoxia and normoxia, for instance within tumor tissue, related to the knowledge that hypoxic areas of tumors may be resistant to chemotherapy and/or radiation therapy.

In some embodiments, introducing a contrast agent of this invention comprises inoculating a subject with cells comprising a nucleic acid encoding a ferritin fusion protein as described above.

In one embodiment, a method of this invention wherein a recombinant ferritin fusion polypeptide has been introduced into a subject, the presence of the ferritin fusion polypeptide enhances image contrast in hypoxic regions thereby identifying regions of hypoxia within a tumor.

In one embodiment, this invention presents a method of non-invasively generating a visible image of a biological sample, the method comprising: (a) providing a MRI contrast enhancement agent comprising: (i) an isolated, recombinant fusion protein comprising a ferritin heavy chain polypeptide fused to a peptide comprising SEQ ID NO: 3, wherein said peptide is fused to the C-terminal end of the ferritin heavy chain polypeptide; and (ii) at least one ferromagnetic magnetite iron oxide; (b) introducing the contrast enhancement agent into a biological sample; and (c) scanning the biological sample using MRI, whereby a visible image of a biological sample is non-invasively generated.

In one embodiment, a contrast agent is comprised in a pharmaceutically acceptable diluent. The term "pharmaceutically acceptable diluent" refers in one embodiment to sterile water. Alternatively, the "pharmaceutically acceptable diluent" can be selected from any of a range of suitable buffers, all of which provide the added advantage of providing a stable pH. Buffers suitable for use in the present invention include phosphate buffers, borate buffers, Tris buffer and HEPES buffer, all of which can further comprise a sterile saline solution. In one embodiment, the pharmaceutically acceptable diluent is phosphate buffer saline.

In one embodiment, the term "a" or "one" or "an" refers to at least one. In one embodiment the phrase "two or more" may be of any denomination, which will suit a particular purpose. In one embodiment, "about" may comprise a deviance from the indicated term of +1%, or in some embodiments, −1%, or in some embodiments, ±2.5%, or in some embodiments, ±5%, or in some embodiments, ±7.5%, or in some embodiments, ±10%, or in some embodiments, ±15%, or in some embodiments, ±20%, or in some embodiments, ±25%.

As used herein, the term "comprising" is intended to mean that the nucleic acids, polypeptides, and methods of use thereof of this invention, include the recited elements, but not excluding others which may be optional. By the phrase "consisting essentially of" it is meant a nucleic acid, polypeptide or method that includes the recited elements but exclude other elements that may have an essential significant effect on the performance of the method. "Consisting of" shall thus mean excluding more than traces of other elements. Embodiments defined by each of these transition terms are within the scope of this invention.

EXAMPLES

Materials and Methods

Expression of PET3A-Ferr and PET28A-Mms6 in *E. coli* Rosetta R3

Ferritin-M6A was cloned into PET28A expression vector and expressed in *E. coli* BL21 codon enriched Rosetta strain to ensure the correct codon usage. An oligomeric ball-shaped ferritin was successfully purified with the Mms6 peptide, M6A, located within the ferritin core, as was verified by mass spectrometry (Data not shown). Ferritin-M6A was incubated with thioglycolic acid to remove endogenous iron and other metals, followed by iron uptake through incubation with buffered ferrous sulfate. To obtain magnetite-loaded Ferritin-M6A (magnetoferritins), ferrous sulfate was added incrementally to heated de-aerated Ferritin-M6A under nitrogen.

Protein Expression and Purification

The expression protocol was as follows: Five to twenty micro liters of bacterial culture (from −80° C.) were transferred to a culture tube containing sterile LB with an appropriate antibiotic. Following this strains of bacterial culture were cultivated with vigorous shaking at 37° C. overnight and the culture with $OD_{600}$ of 0.6-0.8 was used to inoculate a larger volume. Next, the cell pellet of 0.1 L suspension starters was diluted in another tube containing 1 L M9 medium with the same antibiotic, either Choloramphenicol (30 µg/ml) and/or Kanamycin (50 µg/ml) were used. Following this, the culture was grown with vigorous shaking at about 37° C., and growth was continued to $OD_{600nm}$ of 0.6. Then, the expression of plasmid-encoded proteins was induced by 0.5 mM IPTG at 37° C. for five hours.

The purification of His6-Ferritin-M6A purification was as follows: On day 1, the pellet of *E. coli* was stored after expression and centrifugation (as described above). Then, 30 ml of lysis buffer was added and the pellet resuspended by pipetting and vortexing. Following this, cells were lysed by a French Press as is known in the art. A 100 µl aliquot was saved on ice for further analysis. The remaining lysate was centrifuged at 12,000 rpm for 1 hour. The supernatant was collected and a 100 µl aliquot was saved on ice for further analysis. The remaining supernatant was loaded onto a Ni-column, wherein the flow-through volume was saved for analysis. The pellet was also saved for analysis. The column was washed with 100 ml of Washing buffer (200 mM KCl, 20 mM Tris pH 8, 10% Glycerol, 2 Mm T-cep, 40 mM Imidazole), wherein the wash buffer was allowed to flow using gravity. The washing buffer that eluted from the column was saved for analysis. The bound protein was eluted from the column after at least 5 hours incubation of the column beads with 35 ml Elution buffer (200 mM KCl, 20 mM Tris pH 8, 10% Glycerol, 2 Mm T-cep, with 50 mM EDTA and Thrombon (10 unit per 1 mg protein) in 50 ml tubes, at room temperature. SDS-Gel electrophoresis was used to estimate the purity and protein content of the saved samples, e.g., pellet, supernatant that flowed through the column, and Washing buffer after the column Similar fractions having a high protein concentration were combined and further concentrated using a Centricon ultra filtration tube.

Figure 3:
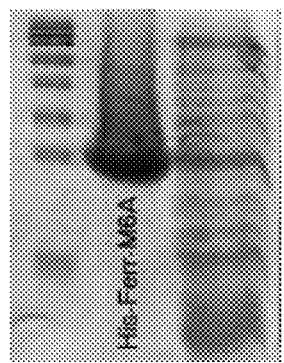
FIG. 3 shows SDS-Polyacrylamide Gel Electrophoresis (SDS-PAGE) of purified His-FerrM6A (lane 2) compared with starting fraction (lane 3). Lane 1 shows size standards.

On day 2, the sample was further purified using size exclusion Fast Protein Liquid Chromatograph as follows: Column: Superdex200; Buffer: 200 mM KCl, 20 mM Tris pH 8.0, 10% Glycerol, 2 Mm T-cep; Flow: 0.5 ml/min; Detection: 280 nm. The purified His-Ferr-M6A protein was analyzed by SDS-PAGE (FIG. 3).

Small Angle X-Ray Scattering (SAXS) Measurements:

SAXS measurements of 10 mg/ml MamM-CTD protein with or without zinc sulfate were performed using the SAXSLAB GANESHA 300-XL system with Cu Kα radiation generated by a sealed microfocused tube (Genix 3D Cu-source with integrated Monochromator) powered at 50 kV and 0.6 mA and three pinholes collimation. The scattering patterns were recorded by a Pilatus 300 K detector. The scattering intensity I(q) was recorded in the interval 0.012<q<0.7 A-1, where q is defined as $$q = \frac{4\pi}{\lambda}\sin\theta,$$

2θ is the scattering angle and λ is the radiation wavelength (1.542 Å). The solution under study was sealed in a thin-walled capillary (glass) of about 1.5 mm diameter and 0.01 mm wall thickness. Measurements were performed under vacuum at a temperature of 4° C. The 2D SAXS images were azimuthally averaged to produce one-dimensional profiles of intensity, I vs. q, using the two-dimensional data reduction program SAXSGUI. The scattering spectra of the capillary and solvent were also collected and subtracted from the corresponding solution data. No attempt was made to convert the data to an absolute scale.

Crystallization and Structure Determination:

Following partial cleavage of His tags used during purification, the purified ferritin-M6A and ferritin were crystallized at different conditions at 20° C. (Table 3 below) in vapor diffusion method. Crystals were harvested with addition of cryo-protecting solution and flash-cooled in liquid nitrogen. Data collections were performed at beamlines ID14-4 at the European Synchrotron Radiation Facility (ESRF), Grenoble, France or at a home source marμX X-ray system (Mar-Research, Germany) equipped with an image plate detector system (MAR 345 mm) Data were reduced and scaled using the HKL2000 suite. Ferritin-M6A phases were obtained using Phaser molecular replacement and PDBcode: 1IES as a template. The final model was built by Coot (Emsley, P. & Cowtan, K. Coot: model-building tools for molecular graphics. Acta crystallographica. Section D, Biological crystallography 60, 2126-32 (2004)) and refined in REFMAC (Vagin, A A, Steiner, R S, Lebedev, A A, Potterton, L, McNicholas, S, Long, F and Murshudov, G N REFMAC5 dictionary: organization of prior chemical knowledge and guidelines for its use. Acta Crystallogr D Biol Crystallogr 60, 2184-2195 (2004)). For Rfree calculation, 5% of the data was excluded. Structural figures were prepared with PyMOL (DeLano, W. L. The PyMOL Molecular Graphics System (DeLano Scientific, San Carlos) 0.99. (2002)).

Transmission Electron Microscopy (TEM)

Horse spleen ferritin was obtained from Sigma. Ferritin was prepared in TRIS buffer. Recombinant fusion protein, Ferritin-M6A, was overexpressed in *E. coli* and purified by Gel-filtration and Ni column chromatography as described above. Pure Ferritin-M6A protein was reconstituted with Fe(II) solution under slow oxidative condition at 60° C. and pH 8.5. TEM Samples were deposited on copper TEM grids (carbon film grids) by placing a 5 μl sample onto the grid for 20 s and then washing the grid with deionized water for 3 s. For samples that were stained to visualize the protein, a 5 μl addition of sodium silicotungstate was placed on the grid for 10 s after the water wash. The grid was then allowed to air dry. In between each step the grid was blotted with filter paper.

Cell Culture

Rat C6 glioma cells were cultured in DMEM medium (Gibco, Invitrogen) supplemented with 10% fetal bovine serum, 2 mM L-glutamine, and penicillin-streptomycin. Puromycin (2 μg/ml) was added to the cell culture medium to select for stably transduced cells. The cells were incubated at 37° C. in a humidified atmosphere of 95% air and 5% $CO_2$.

Construction of C6-pEIRES-HA-Ferretin and C6-pEIRES-HA-Ferretin-M6A Cells

The murine ferritin H-chain cDNA (GENBANK® (GENBANK® is the NIH genetic sequence database, an annotated collection of all publicly available DNA sequences) accession no. NM_010239; SEQ ID NO: 8) further encoding an HA (Influenza Hemagglutinin) tag (HA-ferritin) and having a Kozak sequence (SEQ ID NO: 9) within the 5' untranslated mRNA sequence was generated by RT-PCR. Additionally, a recombinant ferritin-M6A fusion protein was generated in which M6A peptide (SEQ ID NO: 3) was attached to the C-terminus of ferritin to create Ferr-M6A (SEQ ID NO: 6) The nucleic acid sequences encoding these two constructs were cloned into the pEIRES mammalian expression vector.

Figure 10A:
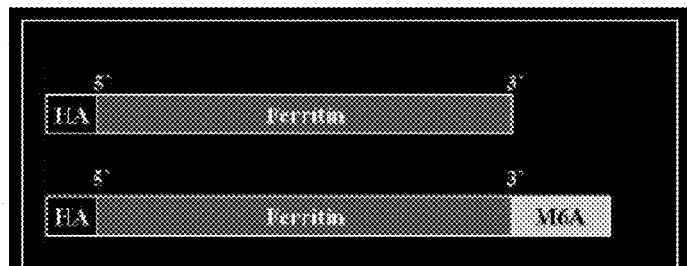
FIG. 10A present schematic diagrams of HA-Ferritin (Ferr; HA-tagged mouse ferritin heavy chain polypeptide; SEQ ID NO: 5) and HA-Ferritin-M6A (Ferr-M6A; HA-tagged mouse ferritin heavy chain polypeptide fused to M6A; SEQ ID NO: 6).
Figure 10B:
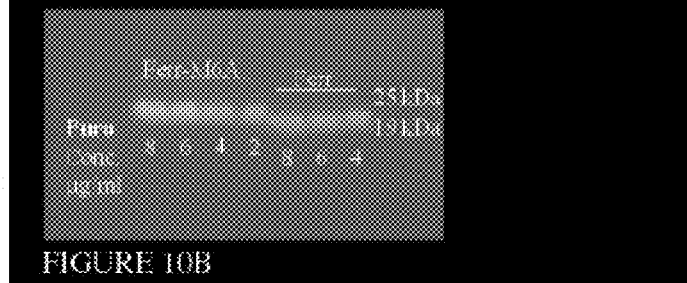
FIG. 10B shows a Western blot analysis from C6 rat glioma cells transfected with either HA-Ferritin or HA-Ferritin-M6A and probed with a Influenza Hemagglutinin (HA) antibody.

Rat C6 glioma cells were transfected with pEIRES HA-ferritin/HA-ferritin-M6A plasmids and stable transfectants selected using puromycin. Ferritin and Ferritin-M6A expression levels were monitored by Western blot analysis (FIG. 10B).

Western Blot Analysis

Cells were lysed in RIPA buffer (20 Mm TRIS pH 7.4, 10% (v/v) glycerol (137 mM), 0.5% (w/v) sodium deoxycholate, 0.1% (w/v) SDS, 1% Triton X-100, 2 mM EDTA, 200 μl of 1 mM PMSF, and protease inhibitor cocktail). Equal amounts of protein (30 μg/lane; Bradford method) were elecrophoresed in a 15 SDS polyacrylamide gel. Gel was transferred to a Western blot membrane and membranes blocked (incubation in 2% BSA in 10 mM Tris-buffered saline, 0.05% Tween (TBST) for 3 hours at 24° C.) and then probed with antibody overnight (incubated overnight at 4° C. with anti-HA monoclonal antibody; HA.11, 1:1000; Covance, Inc., Berkley, Calif.). Membranes were washed 3 times with TBST and incubated with goat-anti-mouse horseradish peroxidase-labeled antibody.

Immunohistochemical and Prussian Blue Staining of Tissue Sections

Tumors were fixed in 4% paraformaldehyde for 15 min followed by thorough washes and processed for immunohistochemical and Prussian blue staining.

Hypoxyprobe-1 (anti-pimonidazole 1/50, Hypoxyprobe Gemini Kit, USA) was used to identify hypoxic tissue areas. Sections were blocked with Dako and incubated for 1 hour at room temperature with biotinylated anti mouse serum proteins (SP). The slides were then incubated with Horseradish Peroxidase (HRP)-conjugated Streptavidin peroxidase, developed with 3,3'-Diaminobenzidine (DAB) and counter-stained with hematoxylin.

For iron detection Prussian blue staining was carried out. Slides with tissue sections were incubated in the working solution by mixing equal parts of 10% potassium ferrocyanide and 20% hydrochloric acid for 40 min. Duplicate slides were additionally treated with DAB, which enhance the sensitivity of iron detection.

In Vitro Hypoxia Test

Rat glioma C6-HA-Ferr and C6-HA-Ferr-M6A cells ($10^5$ cells/well) were grown on untreated 6-well plates either under normoxic (5% $CO_2$, 95% air, 37° C.) and hypoxic (5% $CO_2$, 1% $O_2$, 94% $N_2$, 37° C.) environment for 48 hr. After incubation cells were washed twice with PBS and fixed with 3% paraformaldehyde prepared in PBS.

Prussian Blue Staining on Cells

The cells were incubated in the working solution (a mix of equal parts of 10% potassium ferrocyanide and 20% hydrochloric acid) for 40 min Duplicate wells were additionally treated with DAB for enhancement of the sensitivity of iron detection.

MRI of Cell Suspension

For in vitro MRI measurements, rat C6 glioma cells were transfected with either HA-Ferritin or HA-Ferritin-M6A constructs cloned into the pEIRES vector and stably selected with puromycin. The phantoms were prepared from the cells suspended in various densities in 1% agarose. MRI was acquired from a single coronal slice at Bruker Biospec 9.4 T scanner using Multi-slice multi-echo (MSME) pulse sequence with following parameters: nEchoes=30, TE/TR=8/5000 ms, FOV=4×4 cm, thickness=0.8 mm, NA=2, 256×256. $R_2$ is referred to as the transverse relaxation rate $1/T_2$, where $T_2$ is a decay of transverse magnetization. Exponential fits of signal intensity, I, on a pixel-wise basis as a function of TE were performed to derive $R_2$ relaxation rates and generate $R_2$ maps: $I = I_0 e^{-TE*R2}$. After MRI, cells were isolated and cellular iron content was determined via ICP-MS. Relaxivity, $r_2$, was calculated as the change in $R_2$ as a function of iron content.

In Vivo MRI

MRI was applied for follow up of 4 groups of cd-1 female nude mice (female, 6-9 weeks). The cells containing HA-Ferr and HA-Ferr-M6A constructs were grown in DMEM medium and selected with 2 and 4 µg/ml of puromycin. The cells were trypsinized, washed twice with PBS and counted. The cells were resuspended in PBS to a needed volume with $10^6$ cells per 25 µl. Mice were inoculated subcutaneously above the gluteal muscle with two types of cells ($10^6$ cells/cell type) which contain HA-Ferr and HA-Ferr-M6A constructs. In other words, each cell type, i.e., C6 glioma cells containing either HA-Ferr or HA-Ferr-M6A, was injected above the gluteal muscle of a different leg within the same mouse. Groupings of mice were based on puromycin concentration selection criteria (two groups), which were further subdivided into two more groups with high iron diet (2% carbonyl iron) and with normal diet (5 mice per group). 24 hours before MRI scan the diet of all mice was replaced to normal diet in order to reduce artifacts associated with high iron content in the intestine. Mice were imaged twice: 2 and 3 weeks after inoculation. After 3 weeks from inoculation, the mice were sacrificed and tumors were taken for histology. Two mice from each group were injected i.p. with hypoxia marker Pimonidazole (60 mg/kg) one hour before euthanasia. Results shown are from the group of mice that most closely relate to clinical use, i.e., mice were on a normal diet and the C6 rat glioma cells used in tumor formation were selected with 2 mg/ml puromycin.

MRI measurements were acquired from a single axial slice through the center of the both tumors (HA-Ferr and HA-Ferr-M6A constructs) at 9.4T Bruker spectrometer using a small Quadrature coil (Transceiver 1H 100W). $R_2$ relaxation was measured using multi-spin multi echo (MSME) pulse sequence with 30 echoes (TE=8 ms, TR=3 s, FOV=3×3 cm, slice thickness 0.8 mm, matrix 256×256, number of averages 2). $R_2$ maps were reconstructed on a pixel-wise single exponential fit of the signal intensity decay using equation: $I = I_0 e^{-TE*R2}$, where I is a signal intensity, $I_0$ is proton density and $R2 = 1/T_2$.

Example 1

Recombinant Ferritin:M6A Fusion Protein

Recombinant ferritin:M6A fusion protein was designed and produced from a recombinant fusion nucleic acid encoding an M6A peptide, SEQ ID NO: 3 (12 amino acids from Mms6 protein, FIG. 4, with an N-terminal Glycine added) fused to the C-terminal of a mouse heavy chain ferritin polypeptide (SEQ ID NO: 4). The C-terminus of heavy chain ferritin is located in the inner space of a ferritin particle complex. The resulting ferritin:M6A fusion protein (Ferr-M6a; SEQ ID NO: 6) was designed to facilitate conversion of ferrihydrite into magnetite and by this induce contrast for non-invasive MRI measurements.

Figure 6B:
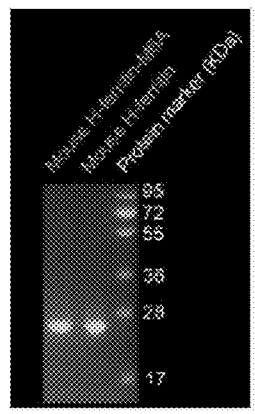

Recombinant fusion protein, ferritin-M6A, was overexpressed in *E. coli* Rosetta R3 cell and purified as shown in FIGS. 5A and 5B, and 6A and 6B. FIGS. 5A and 5B show SDS-PAGE results of the different purification steps identifying the ferritin-M6A at each step. FIG. 6A compares size exclusion chromatography results of the isolated ferritin-M6A fusion protein with purified horse spleen ferritin and purified mouse heavy chain ferritin, demonstrating that all three elute within the same fraction. The ferritin-M6A eluted in a volume fraction corresponding to a 24 mer assembly (ferritin particle) with a molecular weight of 440 KDa, similar to horse spleen ferritin and mouse heavy chain ferritin. FIG. 6B shows the analysis of the corresponding mouse heavy chain ferritin and mouse heavy chain ferritin-M6A peaks.

Example 2

Recombinant Iron Loaded Ferritin M6A Particles

Purified ferritin-M6A fusion protein was reconstituted with Fe(II) solution under slow oxidative condition at 60° C. and pH 8.5. Thus, a magnetic mineral was synthesized within the inner cavity of purified apo-ferritin-N6A.

Figure 7:
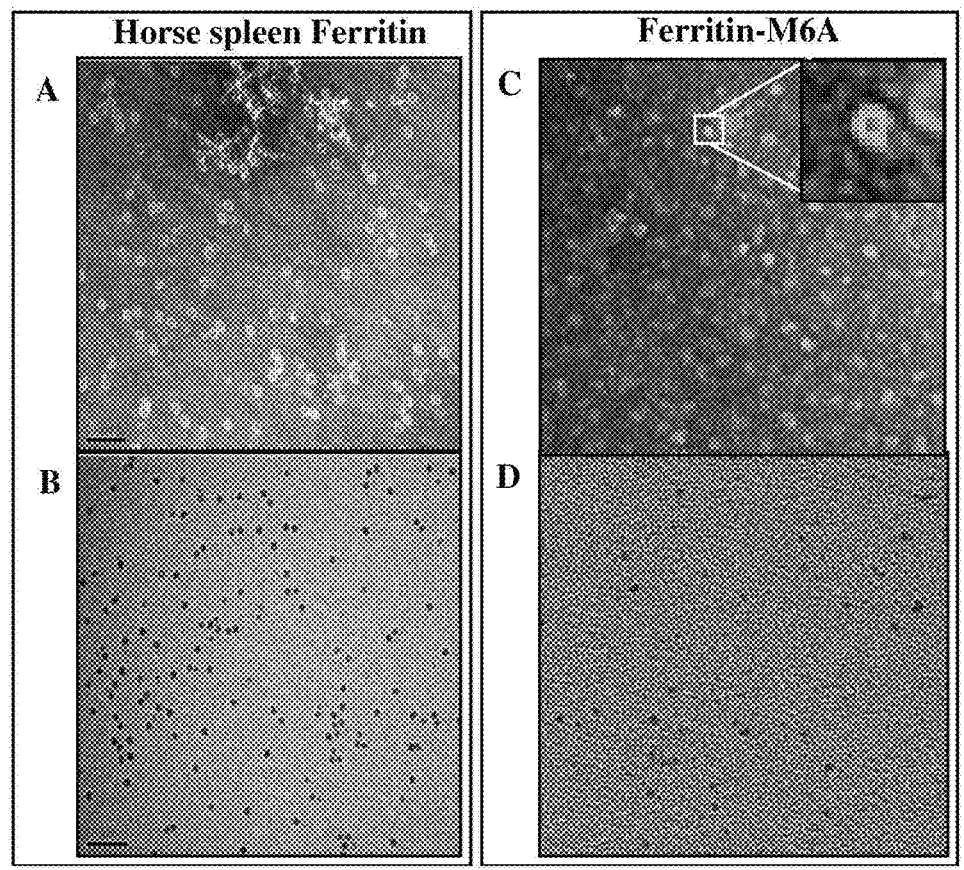
FIGS. 7A, 7B, 7C and 7D show representative TEM images.

Ferritin particle consists of a protein shell of 12 nm in diameter and an iron core of about 6 nm in diameter. In the (transmission electron microscopy) TEM mode, unstained ferritin particles can be discerned as approximately 6 nm black particles, as shown in FIG. 7B, and also negatively stained particles can be discerned as approximately 12 nm white rings encircling a black core, as shown in FIG. 7A. TEM images of recombinant fusion protein, Ferritin-M6A, indicated a well formed spherical hollow shell (FIG. 7C) and entrapped within the shell 6 nm spherical mineral particles (FIG. 7D).

Example 3

In Vitro MRI of Purified Ferritin-M6A

Figure 8:
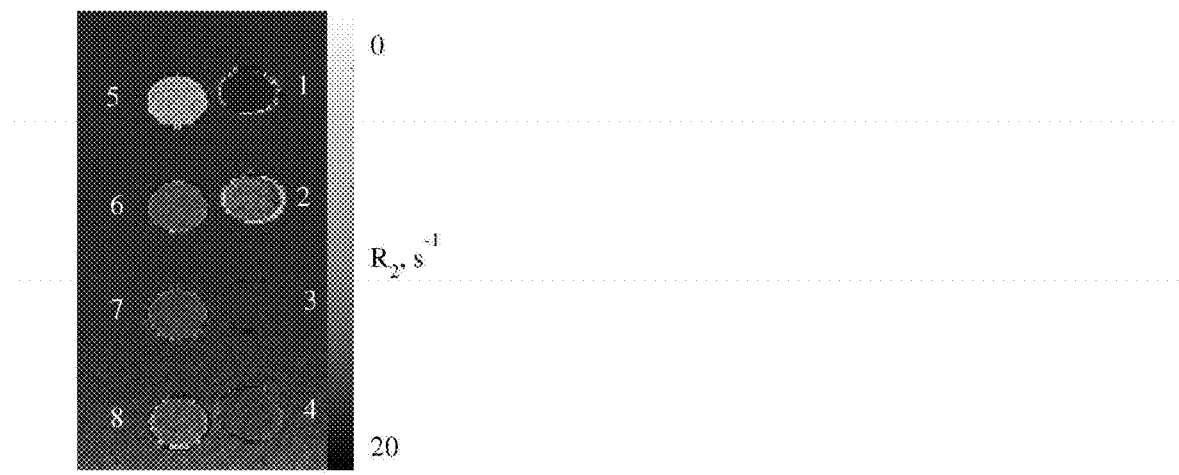
FIG. 8 present MRI contrast images of reconstituted Ferr-M6A and horse spleen ferritin with Fen solution and prepared in AMPSO buffer.

MRI was applied for examination of $R_2$ relaxation of solutions of reconstituted Ferritin-M6A fusion protein and horse spleen ferritin at different concentrations. The $R_2$ relaxation maps, presented in FIG. 8, show significantly higher relaxation rates of Ferritin-M6A fusion protein samples (spots 1 and 2 of FIG. 8) compared with ferritin samples (spots 5-8 of FIG. 8). Table 1 below, provides the $R_2$, $s^{-1}$ numerical values of each sample.

TABLE 1

| | Sample | $R_2$, S-1 |
|---|---|---|
| 1 | Ferritin-M6A 1:1 | 27.6990 |
| 2 | Ferritin-M6A 1:2 | 16.0186 |
| 3 | buffer | 2.8369 |
| 4 | buffer | 2.8671 |
| 5 | Ferritin 4 mg/ml | 6.5245 |
| 6 | Ferritin 2 mg/ml | 4.7055 |
| 7 | Ferritin 1 mg/ml | 3.7548 |
| 8 | Ferritin 0.5 mg/ml | 3.5603 |

Example 4

In Vitro, C6 Cells Overexpressing Ferr-M6A Exhibit Stronger MRI Contrast and Higher Iron Accumulation than Cells Overexpressing Ferr C6 rat glioma cells were transfected with HA-Ferr (SEQ ID NO: 5)/HA-Ferr-M6A (FIG. 9; SEQ ID NO: 6) pEIRES vector and stably selected with puromycin. The HA-Ferr and HA-Ferr-M6A constructs are presented schematically in FIG. 10A. Stable Ferr and Ferr-M6A overexpressions were confirmed by Western blot analysis using mouse monoclonal HA antibody (FIG. 10B).

Figure 11:
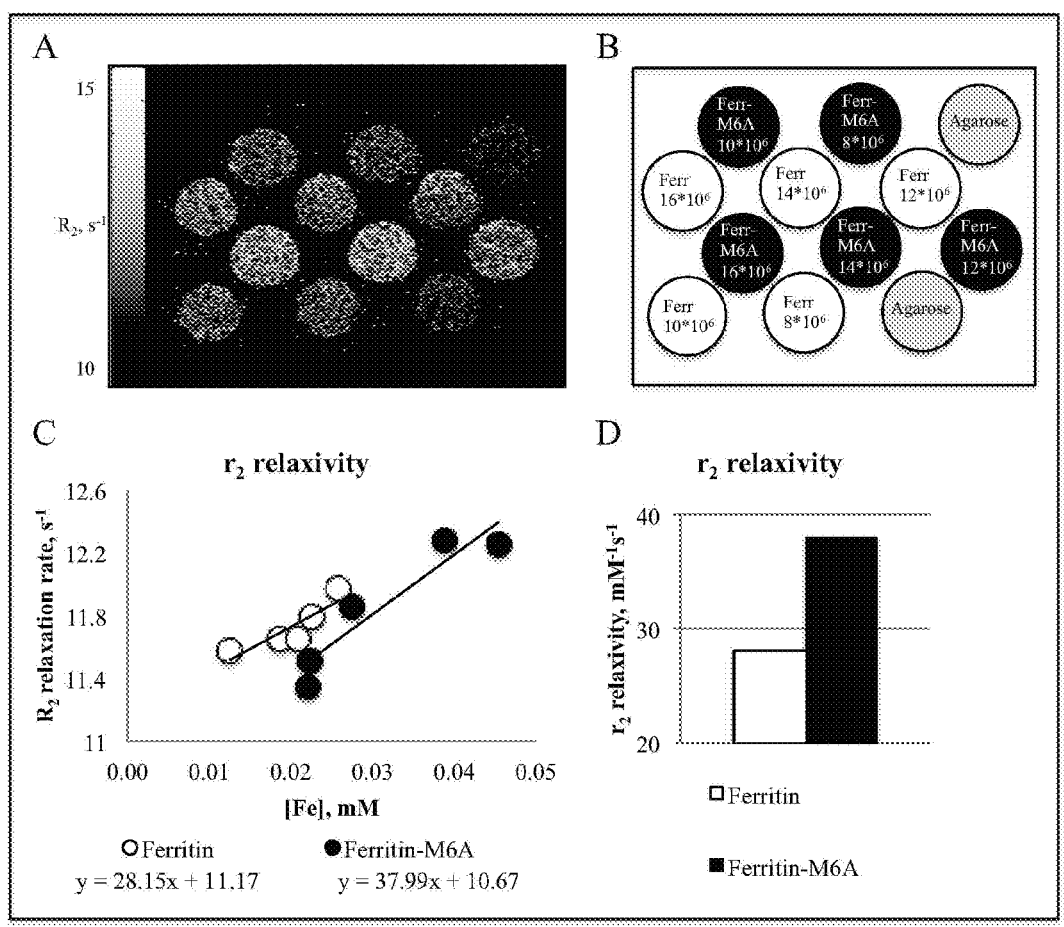
FIGS. 11A, 11B, 11C and 11D show in vitro MRI measurements of rat C6 glioma cells overexpressing either HA-Ferr (labeled as Ferritin or Ferr) or HA-Ferr-M6A (labeled as Ferritin-M6A or Ferr-M6A) constructs.

For in vitro MRI measurements, rat C6 glioma cells were transfected with either HA-Ferritin or HA-Ferritin-M6A constructs cloned into the pEIRES vector and stably selected with puromycin. The phantoms were prepared from the cells suspended in various densities in 1% agarose phantoms. FIG. 11A exhibits $R_2$ map of cell phantoms, whereas FIG. 11B exhibits schematic representation of the location of the phantoms. $R_2$ map demonstrates enhanced $R_2$ relaxation rates that correspond to significant increase of $r_2$ relaxivity in HA-Ferritin-M6A relative to HA-Ferritin.

After MRI, the cells were isolated and cellular iron content was determined via ICP-MS. FIG. 11C shows $r_2$ relaxivity, calculated as a slope of relaxation rates $R_2$ ($1/T_2$) as a function of iron content. FIG. 11D presents a bar graph exemplifying the calculated $r_2$ relaxivity. These results demonstrate the difference in relaxivity per iron, wherein the Ferr-M6A fusion protein shows an enhanced relaxivity.

Example 5

In Vivo MRI of C6 Cells Overexpressing Ferritin and Ferritin-M6A Constructs

Subsequent in vivo studies were performed in order to evaluate the sensitivity of the HA-Ferritin-M6A construct. The cells expressing either HA-Ferritin or HA-Ferritin-M6A construct were grown in DMEM and selected with 2 mg/ml of puromycin. The cells were trypsinized, washed twice in PBS and resuspended in PBS up to $10^6$ cells in 25 ul. CD1-nude female mice (6-9 weeks, n=5) were inoculated subcutaneously above the gluteal muscle of different legs with either HA-Ferritin or HA-Ferritin-M6A cells ($10^6$ cells). Three weeks after inoculation the bearing tumors mice were scanned by MRI. The tumors were removed and analyzed by transmission electron microscopy (TEM) and Prussian blue histological staining.

Figure 12:
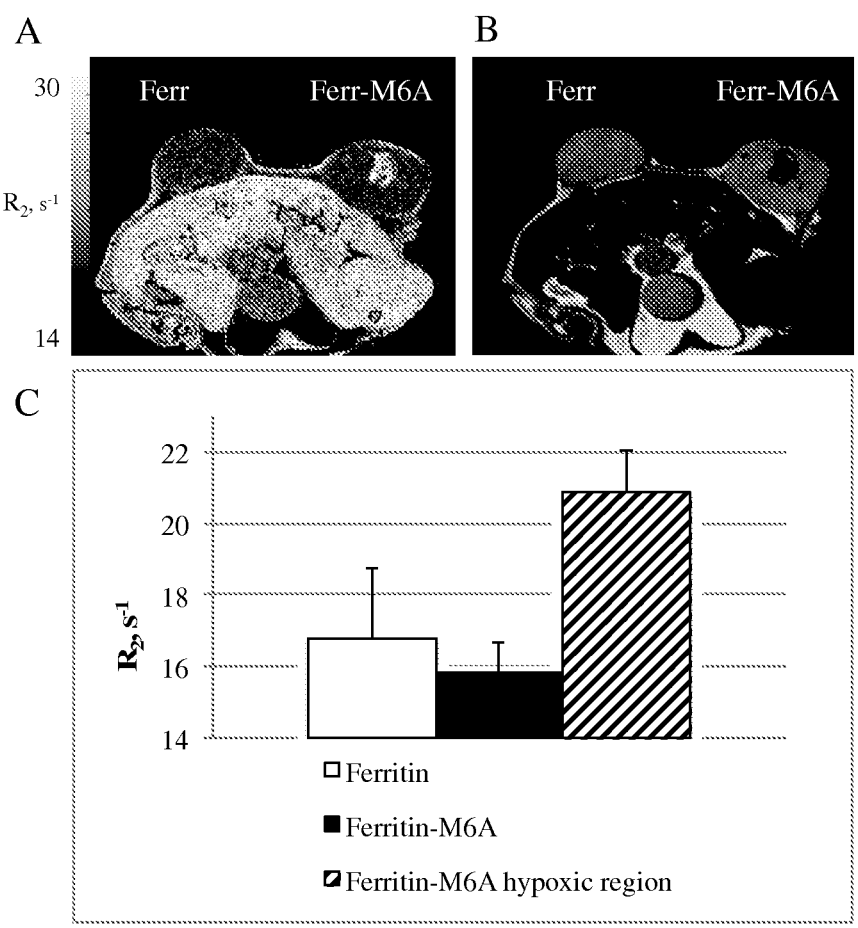
FIGS. 12A, 12B and 12C show in vivo results acquired three weeks post inoculation of C6 glioma cells containing HA-Ferr or HA-Ferr-M6A constructs.
Figure 17:
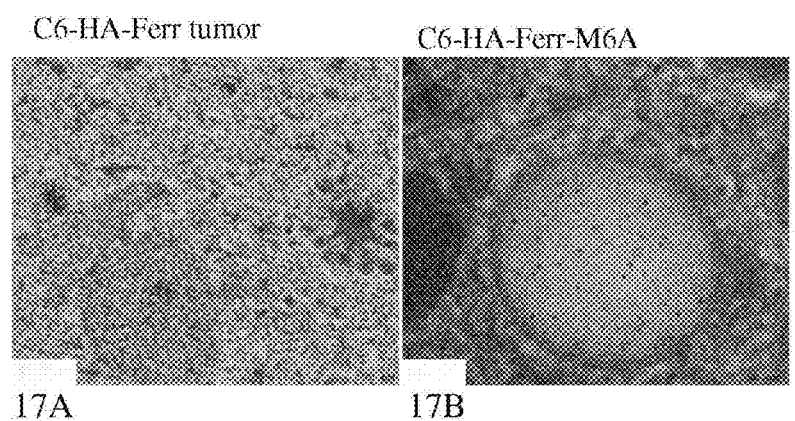
FIGS. 17A and 17B show TEM images from the central part of C6-HA-Ferr and C6-HA-Ferr-M6A tumors, wherein the iron oxide core of the ferritin particles appear as black circle particles of approximately 6 nm.

FIG. 12A shows in vivo $R_2$ maps of an axial slice through the center of C6-HA-Ferr (left) and C6-HA-Ferr-M6A (right) tumors acquired three weeks after the inoculation FIG. 12B represents the corresponding $T_2$ weighted image. Central hypoxic region of C6-HA-Ferr-M6A tumor exhibited elevated MRI contrast. Bar graph of FIG. 12C represents $R_2$ values of region of interests (ROI) tracked C6-HA-Ferr (left) and C6-HA-Ferr-M6A (right) tumors, and the central hypoxic region of C6-HA-Ferr-M6A tumor (n=3). Surprisingly, ROI analysis showed higher $R_2$ relaxation rates for C6 cells overexpressing HA-Ferr compared to cells overexpressing HA-Ferr-M6A (FIG. 12C), while in vitro results were other way around (see FIGS. 11A-D). Notably, the histological analysis revealed significantly higher amounts of iron in the tumors overexpressing HAFerr-M6A construct, especially in the central hypoxic regions of the tumor (FIG. 17).

Whereas, Prussian blue staining of the tumors, which overexpress HA-Ferr construct revealed the presence of low amounts of iron in the peripheral region of tumors. Taken into consideration that for magnetite formation magnetotactic bacteria have to be in low oxygen environment, hypoxic region in the central of the tumor might have a preferable environment for magnetite formation in HA-Ferr-M6A tumors. Thus in the region of hypoxia, M6A freely rotating inside ferritin cavity might interact with iron oxide in order to form magnetite crystals, which enhanced $R_2$ relaxation time in the hypoxic region by 30%. Thus using Ferr-M6A as a hypoxia marker, e.g., a hypoxia reporter, may be beneficial for evaluating clinical strategies and outcomes.

Example 6

Histological Analysis of Subcutaneous C6-Ferr and C6-Ferr-M6A Tumors

Figure 13:
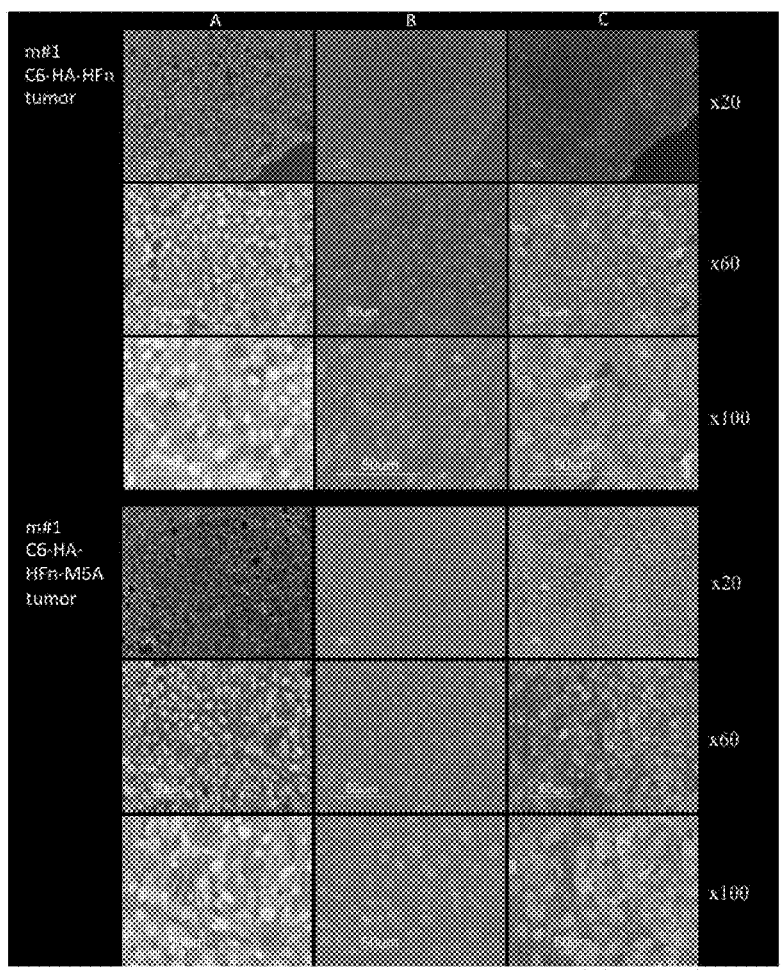
FIG. 13 upper and lower panels show histological analysis of C6-HA-HFn (upper panel) and C6-HA-HFn-M6A (lower panel) tumors stained with (column A) Hematoxylin-Eosin (HE) to examine cell structure; (column B) Prussian blue to evaluate iron accumulation in cells; (column C) Hypoxia immune-staining with anti-pimonidazole and counter stained with Fast red to detect hypoxic regions in the tumors. The cells showed nuclear pleomorphism with foci of tumor necrosis. In both cases tumors showed multifocal areas of iron depositions in their cytoplasm, however iron distribution was much higher in all C6-HA-HFn-M6A tumors. Positive cells showed intra-cytoplasmic blue stains with variable deposits patterns.

Histological examinations with immunohistochemical staining were performed on isolated tumors to validate the hypothesis that hypoxic regions serve a preferable environment for magnetite formation. In order to detect hypoxic regions, one hour before sacrifice, mice were injected i.p. with the hypoxic marker Pimonidazole (60 mg/kg). There weeks after tumor cells inoculation, the mice were euthanized and extracted tumors were taken for histological analysis. FIG. 13 exhibits Hematoxylen-eosin, Prussian blue and immunohistochemical staining with Hypoxi probe. Prussian blue staining was performed in order to detect intracellular iron in tumor cells. HA-Ferr-M6A tumors revealed significantly higher iron content especially in the central parts of the tumors. At the same time the HA-Ferr tumors showed only a small amount of iron, which is mainly concentrated in the peripheral regions of the tumor. The cells showed nuclear pleomorphism with foci of tumor necrosis and vascular proliferation. In both cases tumors showed multifocal areas of iron depositions in their cytoplasm, however iron distribution was much higher in all C6-HA-Ferr-M6A tumors. Positive cells showed intra-cytoplasmic blue stains with variable deposits patterns. In contrast to C6-HA-Ferr tumor cells, those cells overexpressing C6-HA-Ferr-M6A exhibited lipid vacuoles loaded with iron. Imunnohistochemical staining with Hypoxy probe confirmed the disposition of the hypoxic regions of the both tumors. Notably, regions with high iron content according to Prussian blue staining found in HA-Ferr-M6A tumors were confirmed to be hypoxic by immunohistochemistry.

Transmission Electron Microscopy (TEM)

To examine iron content, ferritin core structure and disposition within the cell using higher magnification, we have prepared the samples from the central part of HA-Ferr and HA-Ferr-M6A tumors for TEM examination. Iron oxide core of ferritin appears as black circle particles of approximately 6 nm TEM images (FIGS. 17A and 17B) revealed phospholipid vacuoles loaded with ferritin iron oxide cores in the central parts of HA-Ferr-M6A tumors (FIG. 17B). Although the origin of the vacuoles loaded with ferritin unclear it is in agreement with our histological examination. In contrast, HA-Ferr tumors did not display similar vacuoles and demonstrated low amounts of iron in the peripheral region of the tumors (FIG. 17A).

Figure 16:
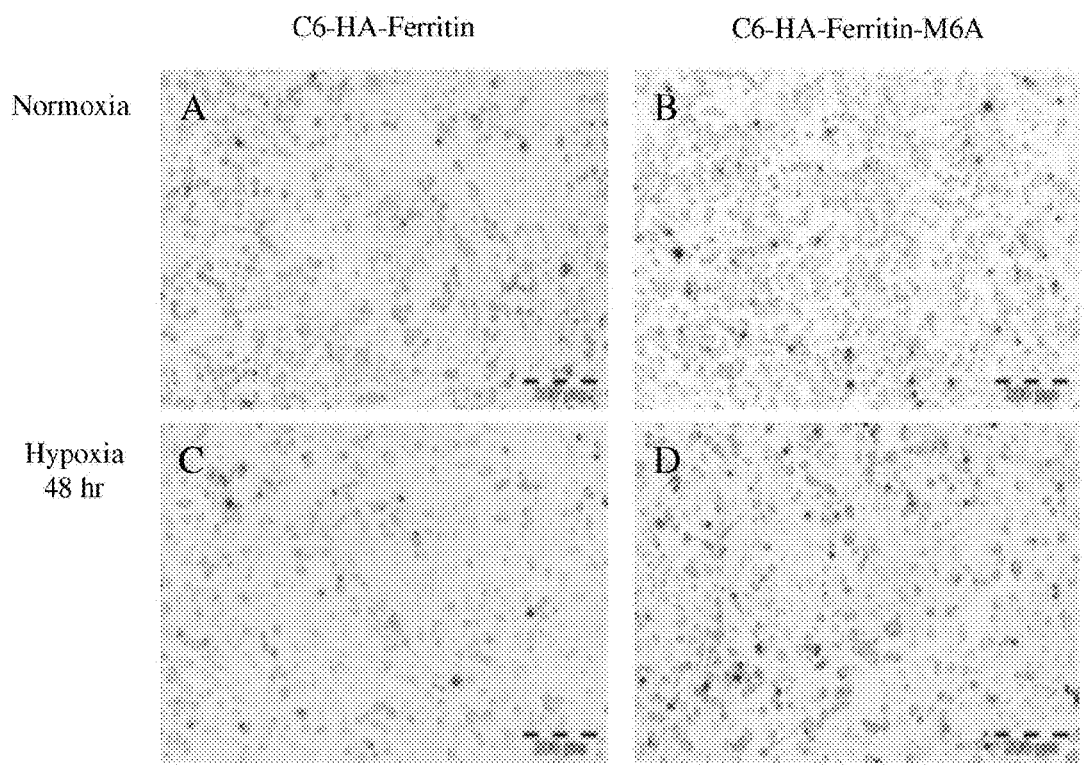
FIGS. 16A, 16B, 16C and 16D show DAB enhanced Prussian blue staining of C6 rat glioma cells overexpressing either HA-Ferr-M6A (16B and 16D) or HA-Ferr (16A and 16C) constructs after incubation of the cells, in vitro, under normoxic (16A and 16B) or hypoxic (16C and 16D) conditions for 48 hours. Intracellular iron is seen as dark spots. Comparison of FIGS. 16A and 16C with FIGS. 16B and 16D shows increased intracellular iron present in cells expressing HA-Ferr-M6A as compared with those expressing HA-Ferr.

In Vitro Examination of Hypoxia, Based on DAB Enhanced Prussian Blue Staining of C6 Rat Glioma Cells Overexpressing Either HA-Ferr-M6A or HA-Ferr Rat C6 glioma cells over-expressing either HA-Ferr-M6A or HA-Ferr construct were incubated under normoxic or hypoxic conditions for 48 hours. Rat C6 glioma cells overexpressing HA-Ferr-M6A exhibited higher iron content both under normoxic (5% $CO_2$, 95% air, 37° C.) (FIG. 16B) and hypoxic (5% $CO_2$, 1% $O_2$, 94% $N_2$, 37° C.) (FIG. 16D) conditions, as compared to their counterparts expressing HA-Ferr (FIGS. 16A and 16C, respectively). The cells were incubated with 4% formalin in PBS and stained with DAB-enhanced Prussian blue staining.

Example 7

SAXS Analysis of Recombinant Fusion Proteins, Ferritin-M6A and Ferritin

Figure 14:
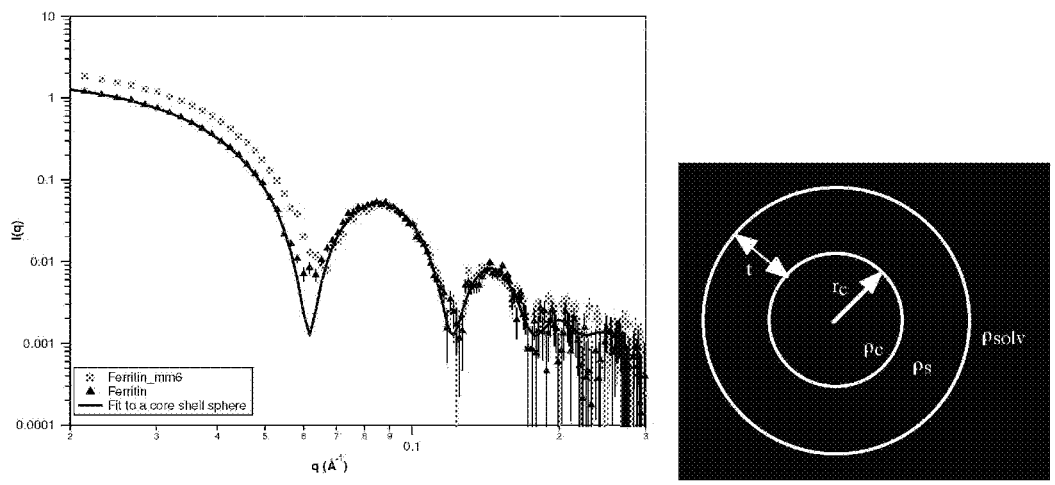
FIG. 14 presents a Small-angle X-ray scattering (SAXS) analysis of purified Ferritin-M6A and Ferritin as spherical core-shell model.

The Small-angle X-ray scattering (SAXS) results of ferritin and ferritin-M6A indicate that both proteins oligomerize into a symmetric homo-oligomeric sphere in solution with the same size of core, shell and envelope as was seen in the crystal structure. Based on the SAXS parameters, ferritin-M6A exhibit higher density in its core although both proteins were purified and kept at the same buffers. This may indicate the presence of the 24 copies of M6A peptide inside the ferritin-M6A core, which is composed of amino acids that are denser then the buffer, as compared to the native ferritin. Table 2 below and FIG. 14 present details of the SAXS analysis results.

TABLE 2

|  | Ferritin-M6A | Ferritin |
| --- | --- | --- |
| scale | 0.102779 ± 350.4 | 0.0995124 ± 333.604 |
| core radius (A) | 36.1074 ± 0.657396 | 37.3099 ± 0.357648 |
| shell thickness (A) | 27.2743 ± 0.767296 | 26.3704 ± 0.452627 |
| Core SLD (A-2) | 9.69108e−06 ± 0.000393908 | 9.50687e−06 ± 7.85696e−05 |
| Shell SLD (A-2) | 1.00115e−05 ± 0.000940172 | 9.96861e−06 ± 0.000852524 |
| Solvent SLD (A-2) | 9.46e−06 ± 0 | 9.46e−06 ± 0 |
| bkg (cm − 1) | 0.00246399 ± 0.000185252 | 0.00125891 ± 0.000102905 |
| chisq | 2748.12 | 314.9 |

TABLE 2-continued

|  | Ferritin-M6A | Ferritin |
| --- | --- | --- |
| Npnts | 102 | 134 |
| Sqrt($X^2$/N) | 5.19061 | 1.53297 |
| Fitted range | [3,104] = 0.0108987 < Q < 0.191691 | [6,139] = 0.0161645 < Q < 0.267167 |

Example 8

Crystallization of Ferritin-M6A and Ferritin

FIG. 18, presents different conditions in which purified ferritin-M6A and ferritin were crystallized, and images of some of the crystals formed.

Table 4 presents the crystallography data of Ferritin M6A

TABLE 4

| Protein | Ferritin-M6A |
| --- | --- |
| Data collection | ID14-4 - ESRF |
| Space group | $P4_22_12$ |
| Cell dimensions |  |
| a, b, c (Å) | 218.15, 218.15, 147.69 |
| α, β, γ (°) | 90, 90, 90 |
| Resolution (Å) | 2.25 |
| Rsym or Rmerge | 14.3 (56.1) |
| I/σI | 10.83 (2.59) |
| Completeness (%) | 95.6 (95.5) |
| Redundancy | 4.7 |
| Wavelength (Å) | 0.947 |
| Refinement |  |
| Resolution (Å) | 2.25 |
| No. reflections | 161908 |

FIG. 15 presents the ferritin-M6A crystallography structure, wherein each color represents a monomer chain out of 12 subunits in the crystallographic asymmetric unit.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A nucleic acid sequence encoding a recombinant ferritin heavy chain fusion protein, comprising a nucleic acid sequence encoding a ferritin heavy chain polypeptide fused to a peptide, wherein said peptide is fused to the C-terminal end of said ferritin heavy chain; said peptide comprising at least a portion of a Mms6 protein sequence and at least one heterologous amino acid at its N-terminal end, wherein said portion of the Mms6 protein sequence is able to bind magnetite, and wherein said portion of the Mms6 protein comprises the amino acid sequence of SEQ ID NO: 2.

2. The nucleic acid sequence of claim 1, wherein said peptide comprises the amino acid sequence of SEQ ID NO: 3.

3. The nucleic acid of claim 1, wherein said ferritin heavy chain polypeptide is a human ferritin heavy chain polypeptide.

4. A vector comprising a nucleic acid according to claim 1.

5. A prokaryotic host cell comprising a vector of claim 4.

6. An in vitro host cell comprising a vector of claim 4.

7. A method of imaging a biological tissue of a subject, comprising the steps of:
   (a) introducing a nucleic acid encoding a recombinant ferritin fusion protein into cells to be imaged- and
   (b) imaging a biological tissue of said subject, which comprises said cells, using a MRI,
wherein said recombinant ferritin fusion polypeptide comprises a ferritin heavy chain polypeptide fused to a peptide, wherein said peptide is fused to the C-terminal end of said ferritin heavy chain; said peptide comprising at least a portion of a Mms6 protein sequence and at least one heterologous amino acid at its N-terminal end, wherein said portion of the Mms6 protein sequence is able to bind magnetite, and wherein said portion of the Mms6 protein comprises the amino acid sequence of SEQ ID NO: 2.

8. The method of claim 7, wherein said peptide comprises the amino acid sequence of SEQ ID NO: 3.

9. The method of claim 7, wherein said cells are used to inoculate said subject.

10. The method of claim 7, wherein said biological tissue is tumor tissue and said introducing comprises administering said nucleic acid or said recombinant ferritin fusion protein to said tumor tissue.

11. The method of claim 7, wherein said subject is on a diet comprising 2% carbonyl iron.

12. The method of claim 7, wherein the presence of said recombinant ferritin fusion polypeptide enhances image contrast.

13. The method of claim 7, wherein said method further comprises tracking cell location in vivo following a cellular based therapy, said cellular based therapy including stem cell therapy, bone marrow transplantation, gene therapy and immune cell therapy.

14. The method of claim 7, wherein said method further comprises identifying normoxic and hypoxic microenvironments within said tissue.

15. The method of claim 7, wherein said tissue is tumor tissue.

16. A method of determining hypoxic microenvironment state of a tumor in a subject, comprising the steps of:
   (a) introducing a nucleic acid encoding a recombinant ferritin fusion protein into a tumor in a subject;
   (b) imaging said tumor, using MRI; and
   (c) evaluating the image for areas of hypoxia and normoxia,
wherein said recombinant ferritin fusion polypeptide comprises a ferritin heavy chain polypeptide fused to a peptide, wherein said peptide is fused to the C-terminal end of said ferritin heavy chain; said peptide comprising at least a portion of a Mms6 protein sequence and at least one heterologous amino acid at its N-terminal end, wherein said portion of the Mms6 protein sequence is able to bind magnetite, and wherein said portion of the Mms6 protein comprises the amino acid sequence of SEQ ID NO: 2.

17. The method of claim 16, wherein said peptide comprises the amino acid sequence of SEQ ID NO: 3.

18. The method of claim 16, wherein said subject is on a diet comprising 2% carbonyl iron.

19. The method of claim 16, wherein the presence of said recombinant ferritin fusion polypeptide enhances image contrast in hypoxic regions thereby identifying regions of hypoxia within the tumor.

* * * * *